United States Patent [19]

Mattingly et al.

[11] Patent Number: 5,145,790
[45] Date of Patent: Sep. 8, 1992

[54] REAGENTS AND METHOD FOR DETECTING POLYCHLORINATED BIPHENYLS

[75] Inventors: Phillip G. Mattingly, Grayslake; R. Jeffrey Brashear, Mundelein, both of Ill.

[73] Assignee: Abbott Laboratories, Abbott Park, Ill.

[21] Appl. No.: 519,039

[22] Filed: May 4, 1990

[51] Int. Cl.$^5$ .......................................... G01N 33/536
[52] U.S. Cl. .................... 436/536; 435/7.9; 435/7.92; 435/7.93; 435/962; 435/968; 436/546; 436/822; 436/825; 549/223
[58] Field of Search ............ 435/7.92, 7.93, 962, 435/968, 7.9; 436/537, 546, 172, 800, 822, 825, 536

[56] References Cited

U.S. PATENT DOCUMENTS

| | | | |
|---|---|---|---|
| 3,766,263 | 10/1973 | Godfrey | 562/465 |
| 4,456,691 | 6/1984 | Stark | 436/822 |
| 4,468,469 | 8/1984 | Atkinson | 436/500 |

OTHER PUBLICATIONS

L. Stanker et al., Chemosphere, vol. 16 (8–9), pp. 1635–1639 (1987).
R. Curry et al., Clinical Chemistry, vol. 25, No. 9, pp. 1591–1595 (1979).
*EPA Method* 608 (*Federal Register* 49 (209) Oct. 26, 1984.
*SW* 8080, Organochlorine Pesticides and PCB's.
Toxicology and Applied Pharmacology, 50:147–155, M. I. Luster, et al., Production and Characterization of Antisera Specific for Chlorinated Biphenyl Species.
*Intern. J. Environ. Anal. Chem.* 10:295–304 (1981), W. H. Newsome, et al., Radioimmunoassay of PCB's in Milk and Blood.
*J. Chem. Soc. (London):* 4257–4258 (1962), J. I. G. Cadogan, A Convenient New Method of Aromatic Arylation.
*Aldrichimica Acta* 21(4): 106–107 (1988), E. K. Yau, et al., Filtering Column Chromatography.
*Tetrahedron* 24:2289–2292 (1967), J. F. W. McOmbie et al., Dimethylation of Aryl Methyl Ethers by Boron Tribromide.
*J. Immunology* 123:1548 (1979), J. F. Kearney, et al., A New Mouse Myeloma Cell Line that has Lost Immunoglobulin Expression.
*Somatic Cell Genetics* 3:231 (1977), Gefter, et al., A Simple Method for Polyethylene Glycol.
A. L. Alford-Stevens, T. A. Bellar, J. W. Eichelberg and W. L. Budde, Characterization of Commercial Aroclors by Automated Mass Spectrometric Determination of Polychlorinated Biphenyls by Level of Chlorination, *Anal. Chem.* 58:2014–2022 (1986).

*Primary Examiner*—Mary E. Ceperley
*Attorney, Agent, or Firm*—Priscilla E. Porembski

[57] ABSTRACT

Reagents and an immunoassay for detecting the presence or amount of polychlorinated biphenyls in a test sample. The assay is performed by adding a known concentration of a tracer labeled with a detectable moiety and a known concentration of an analyte-specific antibody to a test sample to form a mixture, incubating the mixture to form labeled tracer-antibody and analyte-antibody complexes, and determining the presence or amount of tracer-antibody complexes formed as a measure of the presence or amount of analyte in the test sample. Reagents provided include tracers, immunogens and an additive compound useful in preventing non-specific binding of the polychlorinated biphenyls to proteins which may be present in the test sample. A kit for performing the assay also is provided.

13 Claims, No Drawings

REAGENTS AND METHOD FOR DETECTING POLYCHLORINATED BIPHENYLS

BACKGROUND OF THE INVENTION

This invention relates generally to polychlorinated biphenyls, and more particularly, relates to reagents and an immunoassay for detecting the presence or amount of polychlorinated biphenyls in a test sample.

Current Environmental Protection Agency (EPA) approved methodology (EPA method 608, SW 846 method 8080) for determining the presence or amount of polychlorinated biphenyls (PCBs) in a test sample involves extracting the sample with an organic solvent such as hexane or methylene chloride, and then using a gas chromatograph (GC) equipped with an electron capture detector (ECD) to analyze the extract. A more rigorous pretreatment of test sample involving washing with sulfuric acid, mercury desulfurization, or purification on magnesium silicate (Florosil ®, available from Aldrich Chem. Co., Milwaukee, WI) or alumina sometimes is required. The problems encountered with this methodology are inherent to the analytical technique: the procedure is time-consuming and expensive since the GC/ECD runs only one sample at a time, requires 40–60 minutes per test sample, and highly trained technical personnel are required to perform the testing and maintain the equipment.

Various radioimmunoassays (RIAs) for detecting PCBs have been reported. For example, a radioimmunoassay for detecting the commercial PCB mixtures aroclor 1242,1248 and 1254 has been reported in M. I. Luster, et al., *Toxicology and Applied Pharmacology*, 1979, 50, 147–155. In this method, antisera raised in rabbits using three immunogens, haptens 4-amino-4'-chlorobiphenyl, 2-amino-4,5,3',4'-tetrachlorobiphenyl, and 3-amino-2,6,2',6'-tetrachlorobiphenyl were linked via an adipamide linker arm to bovine serum albumin (BSA) and thyroglobulin, and $^{125}I$ tracers used in the method were prepared from the 5-bromovaleramide derivatives of the haptens. Minimum sensitivity of 1–3 ng was reported on standard samples. Feasibility was shown for detecting mixtures of these aroclors in mineral oil.

The detection of PCBs in milk and blood by radioimmunoassay is reported in W. H. Newsome and J. B. Shields, *Intern. J. Environ, Anal. Chem.*, 1981, 10, 295–304. The hapten employed in this assay was 2-amino-2',4,4',5,5'-pentachlorobiphenyl. Antisera was raised in rabbits using a succinamide linking arm to the hapten and the radiotracer was 2-[$^{125}iodo$]-2',4,4',5,5'-pentachlorobiphenyl. The minimum sensitivity reported was 0.1 ng for aroclor 1260. The sensitivity reported for aroclor 1254 was similar, but lower aroclors were not detected with the same sensitivity.

U.S. Pat. No. 4,456,691 to S. Stark teaches the preparation of polyclonal antibodies of PCBs using aroclor 1254 which has been aminated, diazotized and coupled to Bovine Serum Albumin (BSA). The antisera was evaluated by an RIA.

Radioimmunoassays are known to provide sensitive results. However, these assays usually require a higher degree of technical expertise, are more cumbersome that other immunoassay methods, require expensive equipment and involve the handling of radioactive materials.

It would be advantageous to provide an assay which could be used to detect aroclors 1221, 1232, 1242, 1016, 1248, 1254 and 1260 in single assay. It also would be advantageous to provide an assay which did not employ the use of radioisotopes. It further would be advantageous to provide an assay which utilizes a similar sample preparation to that of the EPA method, but can detect the presence or amount of PCBs in the test sample more rapidly and in an automated system.

SUMMARY OF THE INVENTION

The present invention provides a method for detecting the presence or amount of an analyte comprising polychlorinated biphenyls (PCBs) in a test sample. The method comprises the steps of adding a known concentration of a tracer labeled with a detectable moiety and a known concentration of an analyte-specific antibody to a test sample to form a mixture, incubating said mixture under conditions and for a time sufficient to form labeled tracer-antibody and analyte-antibody complexes, and determining the presence or amount of labeled tracer-antibody complexes formed as a measure of the presence or amount of analyte in the test sample. An extraction step may be performed on the test sample. The preferred detectable moiety is fluorescein or a fluorescein derivative. Complexes formed are measured by a fluorescent polarization immunoassay. The method also provides a step wherein a compound is contacted with the mixture to diminish non-specific binding of PCBs and PCB tracer to protein.

Also, the present invention provides hapten compounds, tracer compounds which are used as reagents in the method, immunogen compounds used to raise antibodies for use as reagents in the method, compounds useful for diminishing the non-specific binding of PCBs and the PCB tracer, and a kit for use in the method.

DETAILED DESCRIPTION OF THE INVENTION

The following definitions are applicable to the present invention: The term "determinants", as used herein, refers to those regions of the antigen which are involved in specific binding reactions between antigens and antibodies. In essence, it is the determinants which differentiate antigens, and therefore antibodies, from one another on the basis of immunological specificity.

The term "test sample", as used herein, refers to a sample to be tested for the presence or amount of the analyte of interest. The sample may be in a liquid or solid form, and include soil samples, oil samples, water samples, and other samples which are described in EPA methodology 608, SW 846 method 8080, which is incorporated in its entirety by reference.

The term "analyte", as used herein, refers to a molecule to which a binding member such as an antibody can be obtained or formed. The analyte of interest in the present invention is the class of compounds which are polychlorinated biphenyls of the following structure:

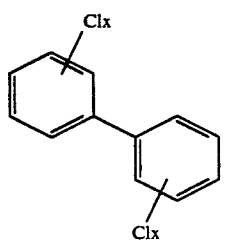

where x=0–5, thus comprising a group of related congeners from mono to decachlorobiphenyl. Such an analyte is a protein-free compound of low molecular weight, generally in the range of from about 50 to about 4000 daltons, more preferably in the range of from about 100 to about 2000 daltons. Such an analyte does not induce antibody formation when injected into an animal but is reactive with antibodies.

The term "analyte-analog", as used herein, refers to a molecule which has substantially the same spatial and polar organization as one or more determinates of the analyte of interest. Such an analyte-analog is a protein-free compound, of low molecular weight, generally in the range of from about 50 to about 4000 daltons, more preferably in the range of from about 100 to about 2000 daltons. This duplication of the determinant(s) enables the analyte-analog to compete with the analyte in the test sample for a binding site on an analyte-specific binding member, such as an antibody. In addition, the analyte-analog can be modified such that it is not identical to the analyte while retaining the necessary determinant(s) for binding to an analyte-specific binding member.

The structure of the analyte-analog determinant(s) need not be identical to that of the analyte; it is sufficient that the analyte-analog substantially duplicate the appropriate determinant(s). Therefore, the analyte-analog can be any molecular structure which contains chemical groups, amino acids, or nucleotides different from those of the analyte, so long as that member (i.e., antibody, receptor, nucleotide sequence, etc.) will recognize and bind to that substantially duplicated determinant(s).

The term "analyte-specific binding member", as used herein, refers to a member, such as an antibody or a receptor, that specifically binds to the analyte. Antibodies, either polyclonal or monoclonal, to such an analyte typically are raised by first conjugating the analyte or analyte-analog to a protein carrier and then injecting the conjugate into an animal. The resulting antibodies can be isolated by conventional, well-known antibody isolation techniques.

The term "tracer", as used herein, refers to an analyte or an analyte-analog which is labeled with a detectable moiety, described hereinafter. The detectable moiety is the signal producing component of the tracer.

In accordance with the method of the present invention, a test sample suspected of containing an analyte of interest is mixed with a labeled tracer and an antibody specific for the analyte and the tracer and incubated. The test sample may be prepared by following EPA-approved extraction methodologies, such as extracting the sample with an organic solvent such as hexane or methylene chloride, as described in EPA method 608, SW 846 method 8080. Any analyte present in the sample and the tracer compete for a limited number of binding sites on the antibody, resulting in the formation of analyte-antibody and tracer-antibody complexes. By maintaining constant the concentration of tracer and antibody, the ratio of the formation of analyte-antibody complex to tracer-antibody complex is directly proportional to the amount of analyte present in the sample.

The preferred detection method is by fluorescence polarization. In this method, the amount of analyte in the sample is determined by exciting the mixture with polarized light and measuring the polarization of the fluorescence emitted by free tracer and tracer-antibody complex. A tracer which is not complexed to an antibody is free to rotate in less than the time required for adsorption and re-emission of fluorescent light. As a result, the re-emitted light is relatively randomly orientated so that the fluorescence polarization of a tracer not complexed to an antibody is low, approaching zero. Upon complexing with a specific antibody, the tracer antibody complex thus formed assumes the rotation of the antibody molecule, which is slower than that of the relatively small tracer molecule, thereby increasing the polarization observed. Therefore, when an analyte competes with the tracer for antibody sites, the observed polarization of fluorescence of the tracer-antibody complex becomes a value somewhere between that of the free tracer and the tracer-antibody complex. If the sample contains a high concentration of the analyte, the observed polarization value is closer to that of the free tracer, i.e., low. If the sample contains a low concentration of the analyte, the polarization value is closer to that of the bound tracer, i.e., high. By sequentially exciting the reaction mixture of an immunoassay with vertically and then horizontally polarized light, and analyzing only the vertical component of the emitted light, the polarization of the fluorescence in the reaction mixture can be accurately determined. The precise relationship between polarization and concentration of the analyte to be determined is established by measuring the polarization values of calibrators having known concentrations. The concentration of the analyte can be interpolated from a standard curve prepared in this manner.

The immunoassay according to the invention is referred to as a homogeneous assay, which means that the final polarization readings are taken from a solution in which bound tracer is not separated from free tracer. This is a distinct advantage over heterogeneous immunoassay procedures, wherein the bound tracer must be separated from the free tracer before a reading can be taken.

Detectable moieties such as chemiluminescent molecules, luminescent molecules, enzymes, and other detectable moieties known to those of ordinary skill in the art may be used in the performance of the invention. In the present invention, the preferred detectable moieties are the luminescent molecules fluorescein and fluorescein derivatives. The choice of the fluorescent molecule for labeling the analyte-analog and thereby forming the tracer is advantageously flexible and is based substantially on the preferences of the routineer. It will readily be appreciated that the fluorescent labels are ideally chosen in accordance with their size, that is, the smaller the molecule, the more rapid it will be able to rotate, and thus the more effective it will be as an fluorescence polarization immunoassay (FPIA) tracer component. These compounds provide fluorescent response when excited by polarized light of an appropriate wavelength and thereby enable the fluorescence polarization measurement. Examples of fluorescein derivatives which can be used in the present invention include fluorescein amine, carboxyfluorescein, α-iodoacetamidofluorescein, 4'-aminomethyl-fluorescein, 4'-N-alkylaminomethylfluorescein, 5-aminomethylfluorescein, 6-aminomethylfluorescein, 2,4-dichloro-1,3,5-triazin-2-yl-aminofluorescein (DTAF), 4-chloro-6-methoxy-1,3,5-triazin-2-yl-aminofluorescein, fluorescein isothiocyanate. Especially preferred derivatives are aminomethylfluorescein and 5-carboxyfluorescein.

Fluorescein exists in two tautomeric forms depending on the acid concentration (pH) of the environment. In the open (acid) form, fluorescein or a fluorescein derivative (or a tracer containing a fluorescent molecule) is capable of absorbing blue light and emitting green fluorescence after an excited state lifetime of about four nanoseconds. When the open and closed forms coexist, relative concentration of molecules in the open and closed forms is easily altered by adjustment of the pH level. Generally, the tracers of the present invention are prepared in solution as biologically acceptable salts such as sodium, potassium, ammonium and the like, which allows the compounds to exist in the open, fluorescent form. The specific salt present will depend on the buffer used to adjust the pH level. For example, in the presence of sodium phosphate buffer, the compounds of the present invention will generally exist in the open form, as a sodium salt.

As used herein, the term "fluorescein", either as an individual compound or as a component of a tracer, is meant to include both the open and closed tautomeric forms, if they exist for a particular molecule, except in the context of fluorescence, in which case an open form is necessary for the fluorescence to occur.

The particular tracers formed in accordance with this invention have been found to produce good assay results, as will be demonstrated in the detailed examples. The concentration of the analyte which can be determined in accordance with the present invention is from about $10^{-6}$ to about $10^{-10}$M. Higher concentration of analyte can be determined by diluting the test sample. Although the concentration range of analyte in the sample will determine the range of concentration of the test reagents such as tracer and antibody, the individual reagent concentrations are determined empirically to optimize the sensitivity of the assay. Suitable concentrations of the tracer and antibody can be ascertained by one of ordinary skill in the art.

Haptens which are structurally similar to polychlorinated biphenyls are prepared for use as immunogens to raise antibodies, and/or analyte-analogs of tracers. Since there are 209 congeners possible in the family of polychlorinated biphenyls, haptens were chosen to resemble selected PCB congeners of the structures below:

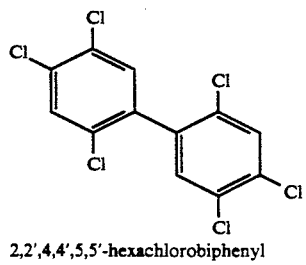

2,2',4,4',5,5'-hexachlorobiphenyl

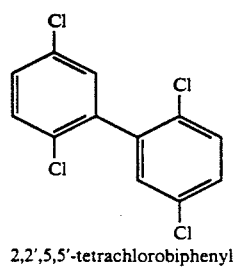

2,2',5,5'-tetrachlorobiphenyl

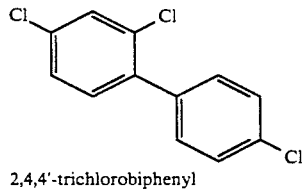

2,4,4'-trichlorobiphenyl

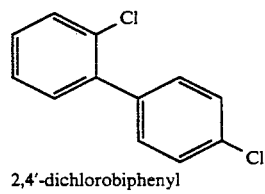

2,4'-dichlorobiphenyl

These are four congeners of some of the more prominent congeners present in the commercial aroclor mixtures. It is contemplated that one of ordinary skill in the art may select other prominent congeners from the family of PCBs on which to base an assay which would behave similarly.

Haptens were prepared to mimic the congeners above by replacing a chloro group with either an amino or hydroxyl group. Both substituted groups have similar size to the chloro group and maintain a lone pair of electrons similar to the chloro group. The amino or hydroxy substituted PCB congeners were prepared by standard methods according to the scheme (I).

SCHEME I:

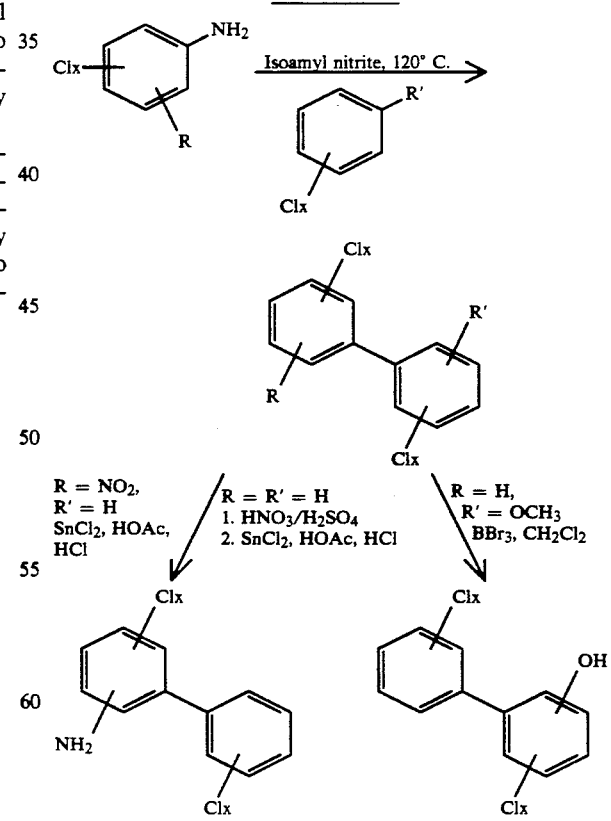

Linker arms were added to the amino or hydroxy substituted PCB congeners according to the scheme (II):

SCHEME II

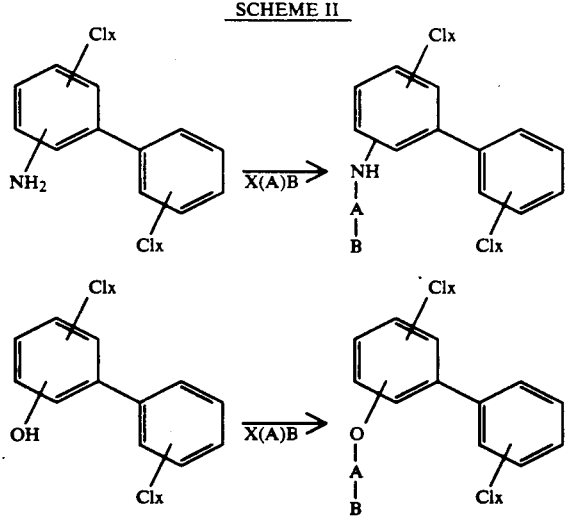

wherein A is a spacer group consisting of from 0 to 50 carbon atoms and heteroatoms, including not more than ten heteroatoms, arranged in a straight or branched chain, saturated or unsaturated, with the proviso that not more than two heteroatoms may be linked in sequence and that branchings may occur only on carbon atoms;

and wherein B is a linking group selected from

—CO₂H

—NH₂

—CHO

—OH and wherein X is a reactive group selected from

Cl—  Br—  I—  CH₃SO₃—

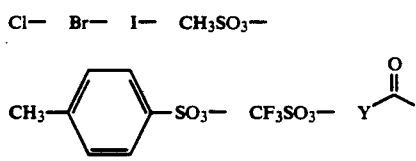

and wherein Y is a carboxyl activating group chosen from

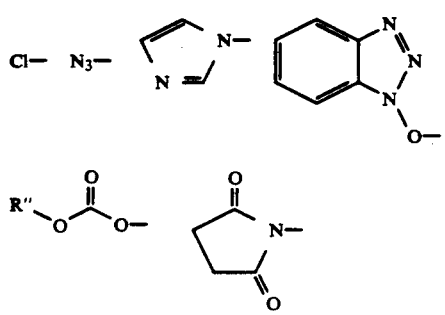

or any other recognized carboxyl activating group known to one of ordinary skill in the art.

When A involves only carbon atoms, it is preferred that A is from 1 to 10 carbon atoms. Suitable heteroatoms include nitrogen, oxygen, sulfur and phosphorus. For example, where A includes nitrogen and oxygen, A could be —CH₂CH=N—O—CH₂—. It appears that compounds with more than two heteroatoms in sequence are less stable.

Alternatively, the amino substituted PCB congeners may be activated directly according to scheme (III).

SCHEME III

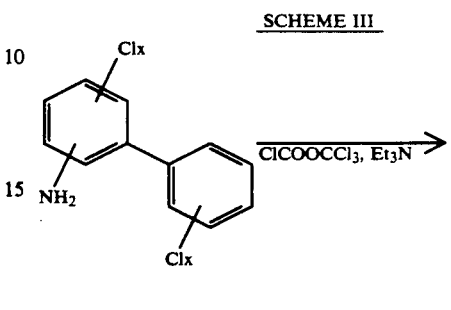

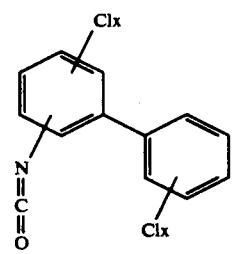

Haptens are prepared according to methods known to those skilled in the art to produce compounds with a side chain containing chemical groups substantially similar to those of the desired determinant(s). These compounds, or their derivatives, are then attached to either a poly(amino acid) carrier or fluorescent molecule.

The antibodies utilized in the present invention were prepared by developing a response in an animal to one to the immunogens described hereinafter. The immunogen was administered and the appropriate antibodies were selected according to methods well-known to those skilled in the art. Although rabbits and mice were the immune hosts used in the experiments described herein, any in vivo host capable of producing antibodies to the immunogens can be used. The antibodies bind with PCBs present in the test sample as well as with the tracer.

Immunogens can be produced from a wide variety of PCB derivatives. The immunogens of the present invention have one of the following general structures:

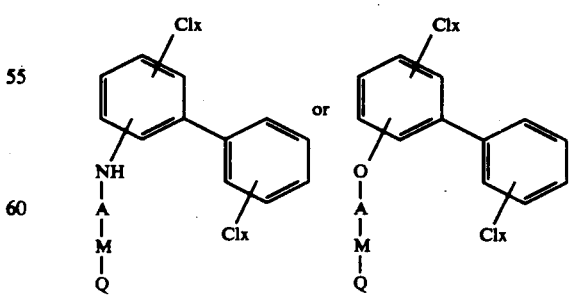

wherein A is a spacer group consisting of from 0 to 50 carbon atoms and heteroatoms, including not more than ten heteroatoms, arranged in a straight or branched chain, saturated or unsaturated, with the proviso that not more than two heteroatoms may be linked in sequence and that branchings may occur only on carbon atoms;

and wherein M is a linking group selected from >C=O, —NH—, O—C=O, N—C=O, N—C=S; and Q is an immunogenic carrier.

A variety of protein carriers can be used as the poly(amino acid) immunogenic carrier. Suitable immunogenic carriers include albumins, serum proteins (e.g., globulins), ocular lens proteins, lipoproteins, and the like. Illustrative protein carriers are BSA, keyhole limpet hemocyanin (KLH), egg ovalbumin, thyroglobulin, and bovine gamma globulin. Alternatively, a suitable derivatized lipopolysaccharide (LPS) or synthetic poly(amino acid) may be utilized.

In the immunogens of the present invention, the chemical bonds between the carboxyl group containing PCB haptens and the amino groups on a protein carrier can be established using a variety of methods known to those skilled in the art. It is frequently preferable to form amide bonds. Amide bonds are formed by first activating the carboxylic acid moiety of the PCB hapten by reaction with an activating reagent such as 1,3-dicyclohexylcarbodiimide and an additive such as N-hydroxysuccinimide. The activated form of the hapten is then reacted with a buffered solution containing the carrier protein. Alternatively, the carboxylic acid hapten may be converted, with or without isolation, into a highly reactive mixed anhydride, acyl halide, acyl imidazolide, or mixed carbonate and then combined with the carrier protein. One of ordinary skill in the art will realize that there are many reagents that can be used to form amide bounds other than those listed.

A PCB hapten with a terminal amine functionality can be transformed into a highly reactive N-hydroxysuccinimide urethane by reaction with N,N'-disuccinimidyl carbonate in a suitable solvent, such as acetonitrile or dimethylformamide. The resultant urethane is then reacted with the carrier protein in a buffered, aqueous solution to provide an immunogen.

A PCB hapten with a terminal aldehyde functionality can be coupled to the carrier protein in a buffered, aqueous solution and in the presence of sodium cyanoborohydride, by reductive amination according the methods known to those skilled in the art.

Alternatively, a PCB hapten containing an alcohol group can be coupled to the carrier protein by first reacting it with phosgene or a phosgene equivalent, such as di-or triphosgene or carbonyldiimidazole, resulting in the formation of a highly reactive chloroformate or imidazoloformate derivative (usually without isolation). The resultant active formate ester is then reacted with the carrier protein in a buffered, aqueous solution to provide an immunogen.

Preferred tracers of the present invention can be produced from a variety of PCB derivatives and have the general structure:

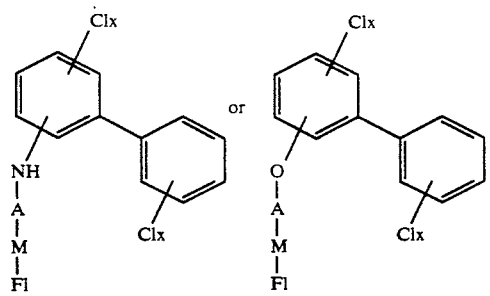

wherein A is a spacer group consisting of from 0 to 50 carbon atoms and heteroatoms, including not more than ten heteroatoms, arranged in a straight or branched chain, saturated or unsaturated, with the proviso that not more than two heteroatoms may be linked in sequence and that branchings may occur only on carbon atoms; and wherein M is a linking group selected from >C=O, —NH—, O—C=O, N—C=O, N—C=S; and wherein Fl is a detectible moiety, preferably fluorescein or a fluorescein derivative.

In the present invention it is preferred that taken together groups A and M consist of 0 to 12 carbon atoms and heteroatoms as described above.

A PCB hapten containing either an amino group or a carboxyl group can be coupled to fluorescein or a fluorescein derivative to prepare the tracers of the present invention. A PCB hapten with a terminal carboxyl group can be coupled to an amino-terminal fluorescein derivative by first activating the carboxylic acid moiety of the PCB hapten by reaction with an activating reagent such as 1,3-dicyclohexylcarbodiimide and an additive such as N-hydroxysuccinimide. The activated form of the hapten is then reacted with a solution of the fluorescein derivative, resulting in the formation of a tracer. Alternatively, the carboxylic acid hapten may be converted, with or without isolation, into a highly reactive mixed anhydride, acyl halide, acyl imidazolide, or mixed carbonate and then combined with the carrier protein. One of ordinary skill in the art will recognize that there are many reagents that can be used to form amide bonds other than those listed.

A PCB hapten with a terminal amine functionality can be transformed into a highly reactive N-hydroxysuccinimide urethane by reaction with N,N'-disuccinimidyl carbonate in a suitable solvent, such as acetonitrile or dimethylformamide. Or, according to Scheme (III), an amino PCB hapten can be activated to an isocyanate. The resultant products are then reacted with an amino fluorescein derivative to form urea tracers. An amino group containing hapten can also be coupled to a carboxyfluorescein derivative which has been activated with N-hydroxysuccinimide in a suitable solvent.

Alternatively, a PCB hapten containing an alcohol group can be coupled to the carrier protein by first reacting it with phosgene or a phosgene equivalent, such as di-or triphosgene or carbonyldiimidazole, resulting in the formation of a highly reactive chloroformate or imidazoloformate derivative (usually without isolation). The resultant active formate ester is then reacted with an amino-terminal fluorescein derivative resulting the formation of a tracer.

Additives which serve to decrease non-specific interaction of PCBs, PCB tracers, and analyte-analogs with proteins, surfaces and the like, include such substances as detergents, organic solvents, and other compounds of the general structure:

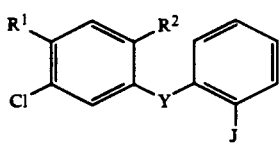

wherein Y is O or NH and one of $R^1$ and $R^2$ is chloro and the other is hydrogen, and J is $CO_2H$ or $CH_2CO_2H$.

The compound preferred for reducing non-specific binding of PCBs and tracers to proteins and surfaces in the present invention is fenclofenac as taught by K. E. Godfrey, U.S. Pat. No. 3,766,263. Although this compound has been employed as an agent to displace thyroid hormones from serum binding proteins, its use in assays for PCBs is not heretofore known. [D. C. Atkinson, et al., U.S. Pat. No. 4,468,469]. Compounds that are related to fenclofenac in their ability to displace thyroid hormones from serum binding proteins have also shown utility in the present invention. In the present invention fenclofenac (Y=O, $R^1$=Cl, $R^2$=H, J=$CH_2CO_2H$) is a preferred compound.

It has been discovered that the tracers and antibodies raised against immunogens of the present invention produce excellent results in a fluorescence polarization assay of the present invention for the semi-quantitative detection of PCBs. However, other assays employing the use of antibodies and antigens also can be used.

The assay of the present invention is performed in accordance with the following general procedure. A known volume of standard or extracted test sample containing or suspected of containing PCBs is delivered to a container such as a test tube. A known concentration of tracer is added to the tube. A known concentration of analyte-specific antibody, produced using the immunogen as described above, also is added to the tube. This reaction mixture is incubated under conditions and for a sufficient time, during which time the tracer and analyte compete for limited antibody binding sites, and whereby tracer-antibody and analyte-antibody complexes form. The amount of tracer-antibody complex formed is measured to determine the presence and/or amount of the analyte in the test sample.

The assay is adaptable to be performed on automated systems such as, but not limited to, the $TD_x$® Therapeutic Drug Monitoring System, the $AD_x$ ™ Abused Drug System, the $IM_x$® Fluorescence Polarization Analyzer and Microparticle Enzyme Immunoassay Analyzer, all of which are available from Abbott Laboratories, Abbott Park, Ill. When either the $TD_x$®, $AD_x$ ™, or the $IM_x$® system is used, the assays are fully automated, from pretreatment to final reading once the test sample has been prepared. Manual assays, however, can also be performed. Although the method of the invention are applicable to manual assays, the automated nature of the $TD_x$®, $AD_x$ ™ and the $IM_x$® systems assures minimal technician time to perform assays and interpret data.

When using fluorescence polarization, the results can be quantified in terms of "millipolarization units", "span" (in millipolarization units) and "relative intensity". The measurement of millipolarization units indicates the maximum polarization when a maximum amount of the tracer is bound to the antibody in the absence of any PCB in the test sample. The higher the net millipolarization units, the better the binding of the tracer to the antibody. For the purposes of the present invention, a net millipolarization value of at least 150 is preferred for a cutoff level of 5 µg/mL of aroclor.

The "span" is an indication of the difference between the net millipolarization and the minimum amount of tracer bound to the antibody. A larger span provides for a better numerical analysis of the data. For the purposes of the present invention, a span of at least 15 millipolarization units is preferred.

The "relative intensity" is a measure of the strength of the fluorescence signal above the background fluorescence. Thus, a higher intensity will give a more accurate measurement. The intensity is determined as the sum of the vertically polarized intensity plus twice the horizontally polarized intensity. The intensity can range from a signal of about three times to about thirty times the background noise, depending upon the concentration of the tracer and other assay variables. For the purposes of the present invention, an intensity of about three to about twenty times that of background noise is preferred.

The pH at which the method of the present invention is practiced must be sufficient to allow the fluorescein moiety of the tracers to exist in their open form. The pH can range from about 4 to 9, preferably from about 6 to 8, and most preferably from about 7 to 7.5. Various buffers can be used to achieve and maintain the pH during the assay procedure. Representative buffers include borate, phosphate, carbonate, Tris, barbital and the like. The choice of the particular buffer used is not critical to the practice of the present invention. However, Tris and phosphate buffers are preferred.

The present invention will now be described by way of specific examples, which are meant to illustrate, but not to limit, the scope of the invention.

EXAMPLES

Synthesis of Haptens

Example 1

2-Amino-2',4,4',5,5'-pentachlorobiphenyl

A. 2',4,4',5,5'-pentachlorobiphenyl was prepared according to the standard procedure of Cadogan [J. I. G. Cadogan, *J. Chem. Soc.* (London), 1962, 4257-58]. Thus, 2,4,5-trichloroaniline (20 g, 0.1 mol) was dissolved in 1,2-dichlorobenzene (125 mL, 1.1 mol). t-Butyl nitrite (28.2 mL, 1.1 mol) was introduce to the stirred solution in three portions over 10 min. After 15 min the evolution of gas had subsided, and the reaction mixture was heated to reflux behind a safety shield for 90 min, and then stirred at ambient temperature for 12 h. The excess 1,2-dichlorobenzene was removed in vacuo and the residue containing the product was purified by filtration through silica gel following the method of E. K. Yau and J. K. Coward, *Aldrichimica Acta*, 1988, 21(4), 106-107, to give after crystallization from ethanol the title product (3 g, 9.3%). Mass spectrum: m/z at 324 for $C_{12}H_5Cl_5$.

B. 2-Nitro-2',4,4',5,5'-pentachlorobiphenyl was prepared according to the standard procedure as described by W. H. Newsome and J. B. Shields [*Intern. J. Environ. Anal. Chem.*, 1981, 10, 295-304]. Thus, 2',4,4',5,5'-pentachlorobiphenyl (2.8 g, 8.9 mmol) was added to a solution of concentrated nitric and sulfuric acid (50 mL, 1:1) at 0° C. with stirring. The reaction was allowed to warm to ambient temperature, then was heated to 60° C.

for 2 h. Finally, after stirring for 48 h at ambient temperature, the reaction mixture was poured into ice (100 g), filtered, and air dried to give the title compound (3 g). Mass spectrum: m/z at 414 for $C_{12}H_4Cl_5NO_2$.

C. 2-Amino-2',4,4',5,5'-pentachlorobiphenyl was prepared from 2-Nitro-2',4,4',5,5'-pentachlorobiphenyl (2.5 g, 6.8 mmol) by dissolving the compound in acetic acid (60 mL) heated to 100° C. and adding a solution of $SnCl_2$ (6 g) in concentrated HCl (30 mL). The temperature was raised to reflux for 3 h, then the reaction mixture was allowed to cool to ambient temperature, whereupon it was poured into ice (100 g). The pH of the solution was adjusted to 9 with NaOH and then extracted with methylene chloride (2×100 mL). The extract was washed with NaOH (1N, 2×25 mL) and water (100 mL); dried over $MgSO_4$ and filtered to give the impure amine. The crude product was chromatographed in two equal batches (Chromatotron®, Harrison Research, Palo Alto, Calif., 4 mm silica gel, step gradient from hexanes to 10% ethyl acetate in hexanes, 20 mL/min) to give the title hapten (830 mg). Mass spectrum: m/z at 340 (M+1) for $C_{12}H_6Cl_5N$.

Example 2

2,4'-Dichloro-4-amino-biphenyl

A. 2,4'-dichloro-4-nitro-biphenyl was prepared by dissolving 2-chloro-4-nitroaniline (2.6 g, 15 mmol) in chlorobenzene (20 mL, 200 mmol), heated to 120° C. under a nitrogen atmosphere. i-Amylnitrite (3.4 mL, 25 mmol) was added to the solution slowly over 1 h via a syringe pump and canula. After stirring for 12 h the reaction mixture was cooled to ambient temperature and the excess chlorobenzene was removed in vacuo. The residue after evaporation was chromatographed by filtration through silica gel as in Example 1A, using mixture of hexane and ethyl acetate (80:20) as the eluent. Further purification was achieved by chromatography [Chromatotron®, 4 mm silica gel, hexanes/methylene chloride, 80:20, 20 mL/min] which yielded the title compound (1.75 g). Mass spectrum: m/z at 267 for $C_{12}H_7Cl_2NO_2$.

B. 2,4'-Dichloro-4-amino-biphenyl was prepared from 2,4'-dichloro-4-nitrobiphenyl (1.75 g, 6.5 mmol) according to the procedure in Example 1C. The crude material was purified by chromatography [Chromatotron®, 4 mm silica gel, hexanes/methylene chloride, 80:20, 20 mL/min] followed by preparative thin layer chromatography [Whatman PLKC18F, 1 mm, 20×20 cm reverse phase plates, methanol/1% aq. acetic acid, 75:25]. Two major components were isolated as oils. The faster eluting component (480 mg) was identified as 2,2'-dichloro-4-aminobiphenyl, while the slower eluting component was the title compound (580 mg). Mass spectrum: m/z at 238 (M+1) for $C_{12}H_9Cl_2N$.

Example 3

2,5,5'-Trichloro-2'-aminobiphenyl

A. 2,5,5'-Trichloro-2'-nitrobiphenyl was prepared according to the procedure in Example 2A from 2-nitro-5-chloroaniline (2.6 g, 15 mmol) and 1,4-dichlorobenzene (29.5 g, 200 mmol). Purification was by filtration through silica gel (see Example 1A) eluting with hexanes/methylene chloride 80:20 yielding the title compound (830 mg). Mass spectrum: m/z at 301 for $C_{12}H_6Cl_3NO_2$.

B. 2,5,5'-Trichloro-2'-aminobiphenyl was prepared from 2,5,5'-trichloro-2'-nitrobiphenyl (830 mg, 2.8 mmol) according to the procedure of example 1C. Purification was by chromatography [Chromatotron®, 2 mm silica gel, ethyl acetate/hexanes, 50:50, 10 mL/min] and yielded the title compound (448 mg). Mass spectrum: m/z at 272 (M+1) for $C_{12}H_8Cl_3N$.

Example 4

5-Hydroxy-2,2',4,4',5'-pentachlorobiphenyl

A. 2,4-Dichloroanisole. 2,4-Dichlorophenol (50 g, 0.3 mol) was dissolved in 2-butanone (500 mL) along with $K_2CO_3$ (200 g), then treated with methyl iodide (90 mL, 1.45 mol) by the dropwise addition over 2 h to the stirred solution. The solution was heated to reflux for 12 h, cooled, filtered, and evaporated. Distillation (Kugelrohr, 5 mm Hg, bT 110° C.) gave the title compound (58 g). Mass spectrum: m/z at 176 for $C_7H_6Cl_2O$.

B. 5-Methoxy-2,2',4,4',5'-pentachlorobiphenyl was prepared from 2,4,5-trichloroaniline (2.95 g, 15 mmol) and 2,4-Dichloroanisole (35 g, 200 mmol) according to the procedure of Example 2A. Distillation of the crude reaction mixture (Kugelrohr, 1 mm Hg, bT 190° C.) gave a mixture of 5-Methoxy-2,2',4,4',5'-pentachlorobiphenyl and 2-Methoxy-2',4,4',5,5'-pentachlorobiphenyl. The isomers were separated by chromatography [Chromatotron®, 4 mm silica gel, heptane, 20 mL/min]. The first eluting isomer was identified as 2-Methoxy-2',4,4',5,5'-pentachlorobiphenyl(383 mg) while the second was the desired 5-Methoxy-2,2',4,4',5'-pentachlorobiphenyl (429 mg). Mass spectrum: m/z at 354 for $C_{13}H_7Cl_5O$.

C. 5-Hydroxy-2,2',4,4',5'-pentachlorobiphenyl was prepared from 5-Methoxy-2,2',4,4',5'-pentachlorophenyl (400 mg, 1.2 mmol) according to the procedure outlined by J. F. W. McOmbie, et al. [*Tetrahedron*, 1967, 24, 2289–92]. Yield: 260 mg. Mass spectrum: m/z at 340 for $C_{12}H_5Cl_5O$.

Example 5

4-Hydroxy-2,2',4',5,5'-pentachlorobiphenyl

A. 2,5-Dichloroanisole was prepared from 2,5-dichlorophenol (50 g, 0.3 mol) according to the procedure in Example 4A. Distillation (bp 98° C., 5 mm Hg) gave the product (52 g). Mass spectrum: m/z at 176 for $C_7H_6Cl_2O$.

B. 4-Methoxy-2,2',4',5,5'-pentachlorobiphenyl was prepared from 2,5-Dichloroanisole (35 g, 200 mmol) and 2,4,5-trichloroaniline (2.95 g, 15 mmol) according to the procedure in Example 2A. The excess dichloroanisole was removed by distillation and the residue was then filtered through silica gel (heptane eluent) and further purified [Chromatotron®, 4 mm silica gel, hexane, 20 mL/min] to give the product (980 mg). Mass spectrum: m/z at 354 for $C_{13}H_7Cl_5O$.

C. 4-Hydroxy-2,2',4',5,5'-pentachlorobiphenyl was prepared from 4-Methoxy-2,2',4',5,5'-pentachlorobiphenyl (950 mg, 2.7 mmol) according to the procedure in Example 4C. Yield: 918 mg. Mass spectrum: m/z at 340 for $C_{12}H_5Cl_5O$.

Example 6

2-Hydroxy-2',4,4',5,5'-pentachlorobiphenyl

A. 3,4-Dichloroanisole was prepared from 3,4-dichlorophenol (50 g, 0.3 mol) according to the procedure in Example 4A. Distillation (bp 75°–80° C., 1 mm Hg) gave the product (56 g). Mass spectrum: m/z at 176 for $C_7H_6Cl_2O$.

B. 2-Methoxy-2',4,4',5,5'-pentachlorobiphenyl was prepared from 3,4-Dichloroanisole (35 g, 200 mmol) and 2,4,5-trichloroaniline (2.95 g, 15 mmol) according to the procedure in Example 2A. The excess dichloroanisole was removed by distillation and the residue was then filtered through silica gel (heptane eluent) and further purified [Chromatotron ®, 4 mm silica gel, cyclohexane, 20 mL/min] to give 2-methoxy-2',4,4',5,5'-pentachlorobiphenyl (700 mg) and 2-Methoxy-2',4',5,5',6-pentachlorobiphenyl (1.2 g). Mass spectrum: m/z at 354 for $C_{13}H_7Cl_5O$.

C. 2-Hydroxy-2',4,4',5,5'-pentachlorobiphenyl was prepared from 42-methoxy-2',4,4',5,5'-pentachlorobiphenyl (700 mg, 2 mmol) according to the procedure in Example 4C. Yield: 295 mg. Mass spectrum: m/z at 340 for $C_{12}H_5Cl_5O$.

Example 7

2-Chloro-4-hydroxybiphenyl

A. 2-Chloro-4-methoxybiphenyl was prepared from p-anisidine (1.85 g, 15 mmol) and chlorobenzene (50 mL) according to the procedure of example 2A. The excess chlorobenzene was removed by distillation and the residue was then filtered through silica gel (cyclohexane/ethyl acetate, 95:5 eluent) to give the product (860 mg). Mass spectrum: m/z at 236 (M+NH$_4$) for $C_{13}H_{11}ClO$.

B. 2-Chloro-4-hydroxybiphenyl was prepared from 4 2-Chloro-4-methoxybiphenyl (437 mg, 2 mmol) according to the procedure in Example 4C. Yield: 408 mg. Mass spectrum: m/z at 204 for $C_{12}H_9ClO$.

Synthesis of Haptens with Linker arms

Example 8

2-Adipamido-2',4,4',5,5'-pentachlorobiphenyl

A. Chloro methyl adipate was prepared from monomethyl adipate (10 g, 62.4 mmol) by refluxing with thionyl chloride (20 mL) for 2 h. Distillation gave the acid chloride (bp 80° C., 0.35 mm Hg, 7.4 g).

B. Methyl 2-Adipamido-2',4,4',5,5'-pentachlorobiphenyl was prepared from 2-Amino-2',4,4',5,5'-pentachlorobiphenyl (300 mg, 0.88 mmol) by treatment with chloro methyl adipate (180 mg, 1 mmol) in pyridine (5 mL) for 12 h at ambient temperature. The mixture was then added to ethyl ether (50 mL) and washed with aq HCl (1.2N, 4×25 mL), saturated NaHCO$_3$ (2×20 mL), brine (2×20 mL) and dried over MgSO$_4$ and filtered. Evaporation gave the product (440 mg). Mass spectrum: m/z at 482 (M+1) for $C_{19}H_{16}Cl_5NO_3$.

C. 2-Adipamido-2',4,4',5,5'-pentachlorobphenyl was prepared by saponification (ethanolic NaOH, reflux, 2 h) to the ester in example 8B. The product was isolated by the addition of ethyl ether (100 mL); washing with aq. HCl (1.2N, 15 mL), brine (20 mL); drying over MgSO$_4$, filtering and evaporating. Yield: 226 mg. Mass spectrum: m/z at 468 (M+1) for $C_{18}H_{14}Cl_5NO_3$.

Example 9

2,4'-Dichloro-4-adipamidobiphenyl

A. Methyl 2,4'-dichloro-4-adipamidobiphenyl was prepared from 2,4'-dichloro-4-amino-biphenyl (300 mg, 1.26 mmol) according to the procedure in example 8B. Yield: 550 mg. Mass spectrum: m/z at 380 (M+1) for $C_{19}H_{19}Cl_2NO_3$.

B. 2,4'-Dichloro-4-adipamidobiphenyl was prepared by saponification (ethanolic NaOH, reflux, 2 h) to the ester as in example 8B. The product was isolated by adding ethyl ether (100 mL); washing with aq. HCl (1.2N, 15 mL), brine (20 mL); drying over MgSO$_4$, filtering and evaporating. Yield: 233 mg. Mass spectrum: m/z at 366 (M+1) for $C_{18}H_{17}Cl_2NO_3$.

Example 10

2,5,5'-Trichloro-2'-adipamidobiphenyl

A. Methyl 2,5,5'-trichloro-2'-adipamidobiphenyl was prepared from 2,5,5'-trichloro-2'-aminobiphenyl (300 mg, 1.1 mmol) according to the procedure in example 8B. Yield: 440 mg. Mass spectrum: m/z at 414 (M+1) for $C_{19}H_{18}Cl_3NO_3$.

B. 2,5,5'-Trichloro-2'-adipamidobiphenyl was prepared by saponificatin (ethanolic NaOH, reflux, 2 h) to the ester as in example 8B. The product was isolated by the addition of ethyl ether (100 mL); washing with aq. HCl (1.2N, 15 mL), brine (20 mL); drying over MgSO$_4$, filtering and evaporating. Yield: 260 mg. Mass spectrum: m/z at 400 (M+1) for $C_{18}H_{16}Cl_3NO_3$.

Example 11

5-(Methoxycarboxylato)-2,2',4,4',5'-pentachlorobiphenyl

A. Ethyl5-(methoxycarboxylato)-2,2',4,4',5'-pentachlorobiphenyl was prepared from 5-hydroxy-2,2',4,4',5'-pentachlorobiphenyl (200 mg, 0.58 mmol, Example 4C) and ethyl bromoacetate (80 μL, 0.73 mmol) by dissolving both in 2-butanone (10 mL) in the presence of K$_2$CO$_3$ (100 mg, 0.725 mmol) and a catalytic amount of NaI. The reaction mixture was stirred under a nitrogen atmosphere at reflux for 16 h; cooled; diluted with ethyl ether; washed with H$_3$PO$_4$ (1.4M, 50 mL) and brine (25 mL); dried over MgSO$_4$; and evaporated to give the product. Mass spectrum: m/z at 446 (M+NH$_4$) for $C_{16}H_{11}Cl_5O_3$.

B. 5-(Methoxycarboxylato)-2,2',4,4',5'-pentachlorobiphenyl was prepared by saponification of ethyl 5-(methoxycarboxylato)-2,2',4,4',5'-pentachlorobiphenyl using methanolic KOH (20 mL, 200 mg) at ambient temperature for 5 h. The solution was then evaporated and the residue suspended in H$_3$PO$_4$ (1.4M, 25 mL); extracted with ethyl ether (4×25 mL); the extract was washed with brine (25 mL); dried over MgSO$_4$; and evaporated to give the product. Mass spectrum: m/z at 416 (M+NH$_4$) for $C_{14}H_7Cl_5O_3$.

Example 12

4-(Methoxycarboxylato)-2,2',4',5,5'-pentachlorobiphenyl

A. Ethyl 4-(methoxycarboxylato)-2,2',4',5,5'-pentachlorobiphenyl was prepared from 4-hydroxy-2,2',4',5,5'-pentachlorobiphenyl (650 mg, 1.9 mmol, Example 5C) by the method in example 11A. Purification by chromatography [Chromatotron ®, 2 mm silica gel, 5% ethyl acetate in cyclohexane, 10 mL/min] yielded the title compound (715 mg). Mass spectrum: m/z at 446 (M+NH$_4$) for $C_{16}H_{11}Cl_5O_3$.

B. 4-(Methoxycarboxylato)-2,2',4',5,5'-pentachlorobiphenyl was prepared from Ethyl 4-(methoxycarboxylato)-2,2',4',5,5'-pentachlorobiphenyl (700 mg, 1.65 mmol) by the method of example 11B (520 mg). Mass spectrum: m/z at 416 (M+NH$_4$) for $C_{14}H_7Cl_5O_3$.

Example 13

2-(Methoxycarboxylato)-2',4,4',5,5'-pentachlorobiphenyl

A. Ethyl 2(methoxycarboxylato)-2',4,4',5,5'-pentachlorobiphenyl was prepared from 2-hydroxy-2',4,4',5,5'-pentachlorobiphenyl (295 mg, 0.86 mmol, Example 6C) by the method in example 11A (438 mg). Mass spectrum: m/z at 446 (M+NH$_4$) for C$_{16}$H$_{11}$Cl$_5$O$_3$.

B. 2-(Methoxycarboxylato)-2',4,4',5,5'-pentachlorobiphenyl was prepared from Ethyl 2-(methoxycarboxylato)-2',4,4',5,5'-pentachlorobiphenyl (438 mg) by the method of example 11B (200 mg). Mass spectrum: m/z at 416 (M+NH$_4$) for C$_{14}$H$_7$Cl$_5$O$_3$.

Example 14

4-(Butoxy-4-carboxylato)-2-chlorobiphenyl

A. Ethyl 4-(butoxy-4-carboxylato)-2-chlorobiphenyl was prepared from 2-chloro-4-hydroxybiphenyl (408 mg, 2.0 mmol, Example 6C) and ethyl 4-bromobutyrate (290 mL, 2.05 mmol) by the method in example 11A. Purification by chromatography [Chromatotron ®, 4 mm silica gel, 10% ethyl acetate in cyclohexane, 20 mL/min] yielded the title compound (585 mg). Mass spectrum: m/z at 319 (M+1), 336 (M+NH$_4$) for C$_{18}$H$_{19}$Cl$_1$O$_3$.

B. 4-(Butoxy-4-carboxylato)-2-chlorobiphenyl was prepared from ethyl 4-(butoxy-4-carboxylato)-2-chlorobiphenyl (585 mg, 1.8 mmol)) by the method of example 11B (462 mg). Mass spectrum: m/z at 308 (M+NH$_4$) for C$_{16}$H$_{15}$Cl$_1$O$_3$.

Synthesis of Immunogens

Example 15

A. General procedure I: The hapten (25 mg) was activated with dicyclohexylcarbodiimide (DCC, 15 mg, 0.07 mmol) and N-hydroxysuccinimide (NHS, 25 mg, 0.2 mmol) in tetrahydrofuran (5 mL, freshly distilled from benzophenone ketyl) at 0° C. for 2 h and at ambient temperature for 12 h under a nitrogen atmosphere. Bovine serum albumin (BSA, 200 mg) was dissolved in phosphate buffer (10 mL, 0.1M, pH 8.0). The solution of the activated hapten was filtered through a plug of glass wool into the stirred solution of the BSA. Stirring was continued for 24 h, after which the reaction mixture was transferred to dialysis tubing (molecular weight cutoff: 15,000) and dialysed against ammonium formate (6 L, 0.1N) at 4° C. for 48 h. The dialysate was lyophilized to give a solid which was then washed with chloroform (25 mL) and dried in vacuo over P$_2$O$_5$. By UV the immunogen contained 13-26 moles of hapten per mole of BSA.

B. General procedure II: The hapten (25 mg) was dissolved in thionyl chloride (1 mL) and heated to 60° C. for 12 h. Afterwards the excess thionyl chloride was removed in vacuo, leaving the acid chloride of the hapten. The acid chloride was then dissolved in THF (2 mL, freshly distilled from benzophenone ketyl). BSA (200 mg) was dissolved in phosphate buffer (10 mL, 0.1M, pH 8.0) and cooled to 0° C. The solution of the acid chloride was added at once with stirring, along with more THF (8 mL). Stirring was continued for 2 h at ambient temperature, afterwhich the reaction mixture was transferred to dialysis tubing (molecular weight cutoff: 15,000) and dialysed against ammonium formate (6 L, 0.1N) at 4° C. for 48 h. The dialysate was lyophilized to give a solid which was then washed with chloroform (25 mL) and dried in vacuo over P$_2$O$_5$. By UV the immunogen contained 13-26 moles of hapten per mole of BSA.

Example 16

(2-Adipamido-2',4,4',5,5'-pentachlorobiphenyl)$_x$BSA was prepared from 2-Adipamido-2',4,4',5,5'-pentachlorobiphenyl (example 8C) by the procedure in example 15A.

Example 17

(2,4'-dichloro-4-adipamidobiphenyl)$_x$BSA was prepared from 2,4'-dichloro-4-adipamidobiphenyl (Example 9B) by the procedure in example 15A.

Example 18

(2,5,5'-Trichloro-2'-adipamidobiphenyl)$_x$BSA was prepared from 2,5,5'-trichloro-2'-adipamidobiphenyl (Example 10B) by the procedure in example 15A.

Example 19

[5-(Methoxycarboxylato)-2,2',4,4',5'-pentachlorobiphenyl]$_x$BSA was prepared from 5-(Methoxycarboxylato)-2,2',4,4',5'-pentachlorobiphenyl (Example 11B) by the procedure in example 15B.

Example 20

[4-(methoxycarboxylato)-2,2',4',5,5'-pentachlorobiphenyl]$_x$BSA was prepared from 4-(methoxycarboxylato)-2,2',4',5,5'-pentachlorobiphenyl (Example 12B) by the procedure in example 15B.

Example 21

[2-(methoxycarboxylato)-2',4,4',5,5'-pentachlorobiphenyl]$_x$BSA was prepared from 2-(methoxycarboxylato)-2',4,4',5,5'-pentachlorobiphenyl (Example 13B) by the procedure in example 15B.

Example 22

[4-(Butoxy-4-carboxylato)-2-chlorobiphenyl]$_x$BSA was prepared from 4-(Butoxy-4-carboxylato)-2-chlorobiphenyl (Example 14B) by the procedure in example 15A.

Synthesis of Tracers

Example 23

A. General procedure I: The hapten (25 mg) was activated with dicyclohexylcarbodiimide (DCC, 15 mg, 0.07 mmol) and N-hydroxysuccinimide (NHS, 25 mg, 0.2 mmol) in tetrahydrofuran (5 mL, freshly distilled from benzophenone ketyl) or dimethyl formamide (5 mL) at 0° C. for 2 h and at ambient temperature for 12 h under a nitrogen atmosphere. To an aliquot (1 mL) of the activated hapten was added an amino bearing fluorescein derivative (4 mg) along with 2 drops of triethylamine. The reaction mixture was stirred for 12 h, evaporated and chromatographed [Whatman PLKC18F, 1 mm, 20×20 cm reverse phase plates, methanol/1% aq. acetic acid, 60:40 or MERCK Silica Gel 60 F-254, 2 mm, 20×20 cm, chloroform/methanol, 85:15].

B. General procedure II: The hapten (25 mg) was dissolved in thionyl chloride (1 mL) and heated to 60° C. for 12 h. Afterwards the excess thionyl chloride was removed in vacuo, leaving the acid chloride of the hapten. The acid chloride was then dissolved in THF (5 mL, freshly distilled from benzophenone ketyl). To an aliquot (1 mL) of the activated hapten was added an amino bearing fluorescein derivative (4 mg) along with 2 drops of triethylamine. The reaction mixture was stirred for 12 h, evaporated and chromatographed [Whatman PLKC18F, 1 mm, 20×20 cm reverse phase plates, methanol/1% aq. acetic acid, 60:40 or MERCK Silica Gel 60 F-254, 2 mm, 20×20 cm, chloroform/methanol, 85:15].

C. General procedure III: The amino bearing hapten was converted to its hydrochloride by treatment with ethereal hydrogen chloride. The hapten hydrochloride (50 mg) was dissolved in THF (10 mL, freshly distilled from benzophenone ketyl) and treated with trichloromethyl chloroformate (100 μL) for 30 min under a nitrogen atmosphere. Afterwards the volatiles were removed in vacuo and the residue was taken up in DMF, divided into aliquots and treated with an amino bearing fluorescein derivative along with one drop of triethylamine. After stirring for 12 h, the reaction mixture was evaporated and chromatographed [Whatman PLKC18F, 1 mm, 20×20 cm reverse phase plates, methanol/1% aq. acetic acid, 60:40 or MERCK Silica Gel 60 F-254, 2 mm, 20×20 cm, chloroform/methanol, 85:15].

Example 24

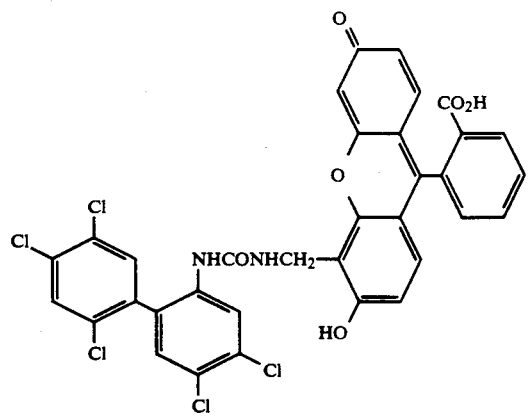

EXAMPLE 25

A tracer with the following structure was prepared from 2-Amino-2',4,4',5,5'-pentachlorobiphenyl (Example 1C) and 4'-(N-glycylaminomethyl)-fluorescein according to the method in Example 23C. Mass spectrum (FAB): m/z at 784 (M+1) for $C_{36}H_{22}Cl_5N_3O_7$.

A tracer with the following structure was prepared from 2-Amino-2',4,4',5,5'-pentachlorobiphenyl (Example 1C) and 4'-aminomethyl fluorescein according to the method in Example 23C. Mass spectrum (FAB): m/z at 727 (M+1) for $C_{34}H_{19}Cl_5N_2O_6$.

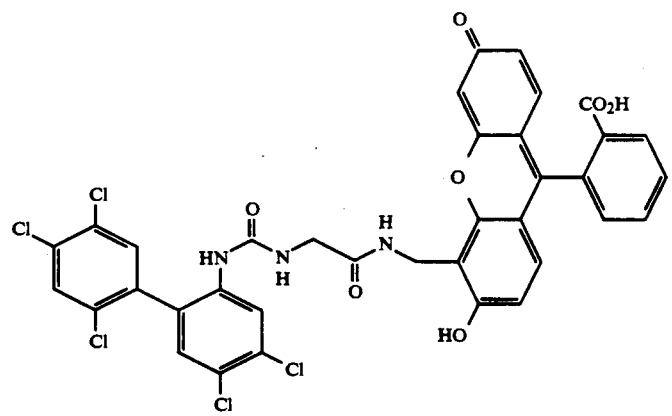

EXAMPLE 26

A tracer with the following structure was prepared from 2-Amino-2',4,4',5,5'-pentachlorobiphenyl (Example 1C) and 5-[N-(2-aminoethyl)carboxamido]-fluorescein according to the method in Example 23C. Mass spectrum (FAB): m/z at 784 (M+1) for $C_{36}H_{22}Cl_5N_3O_7$.

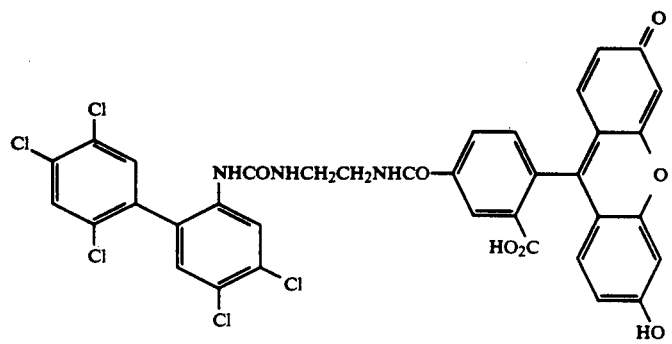

EXAMPLE 27

A tracer with the following structure was prepared from 2,4'-dichloro-4-aminobiphenyl (Example 2B) and 4'-aminomethyl fluorescein according to the method in Example 23C. Mass spectrum (FAB): m/z at 625 (M+1) for $C_{34}H_{22}Cl_2N_2O_6$.

EXAMPLE 30

A tracer with the following structure was prepared from 2,5,5'-trichloro-2-aminobiphenyl (Example 3B) and 4'-aminomethyl fluorescein according to the method in Example 23C. Mass spectrum (FAB): m/z at 681 (M+Na) for $C_{34}H_{21}Cl_3N_2O_6$.

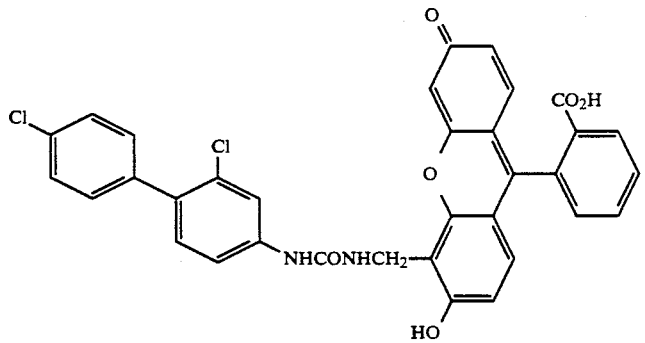

EXAMPLE 28

A tracer with the following structure was prepared from 2,4'-dichloro-4-aminobiphenyl (Example 2B) and 4'-(N-glycylaminomethyl)-fluorescein according to the method in Example 23C. Mass spectrum (FAB): m/z at 682 (M+1) for $C_{36}H_{25}Cl_2N_3O_7$.

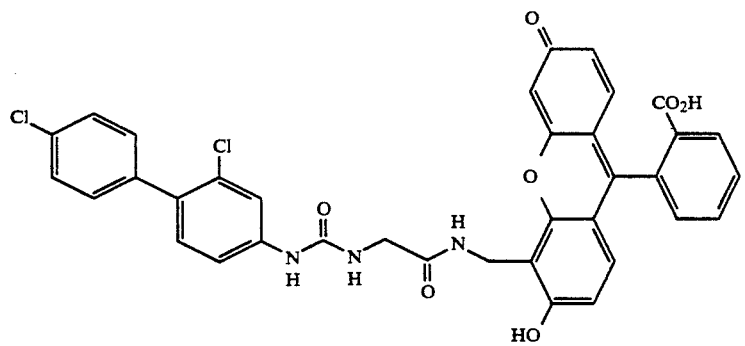

EXAMPLE 29

A tracer with the following structure was prepared from 2,4'-dichloro-4-aminobiphenyl (Example 2B) and 5-[N-(2-aminoethyl)carboxamido]-fluorescein according to the method in Example 23C. Mass spectrum (FAB): m/z at 682 (M+1) for $C_{36}H_{25}Cl_2N_3O_7$.

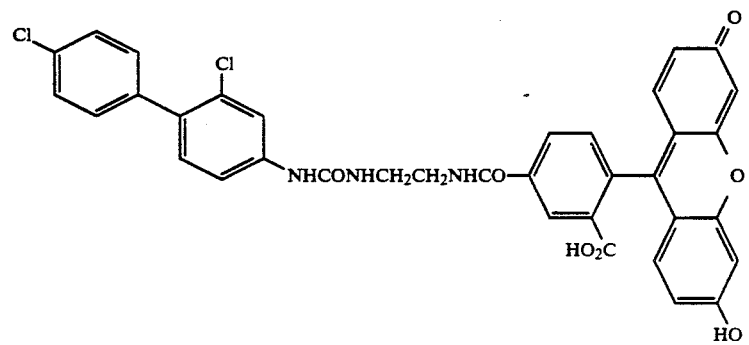

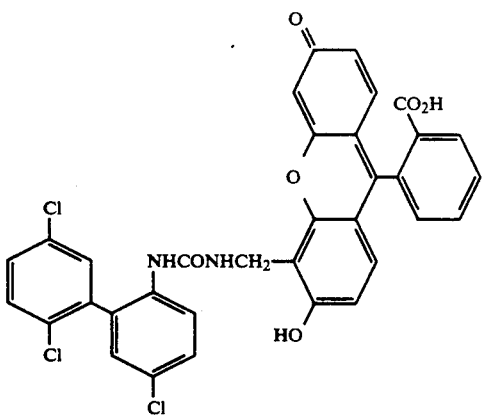
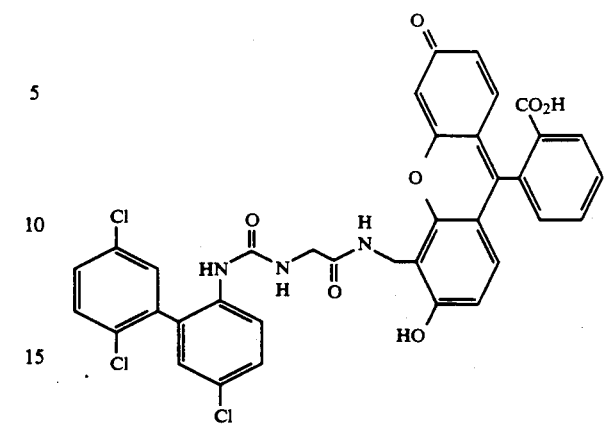

EXAMPLE 31

A tracer with the following structure was prepared from 2,5,5'-trichloro-2'-aminobiphenyl (Example 3B) and 4'-(N-glycylaminomethyl)-fluorescein according to the method in Example 23C. Mass spectrum (FAB): m/z at 716 (M+1) for $C_{36}H_{24}Cl_3N_3O_7$.

EXAMPLE 32

A tracer with the following structure was prepared from 2,5,5'-trichlor-2'-aminobiphenyl (Example 3B) (Example 2B) and 5-[N-(2-aminoethyl)carboxamido]-fluorescein according to the method in Example 23C. Mass spectrum (FAB): m/z at 716 (M+1) for $C_{36}H_{24}Cl_3N_3O_7$.

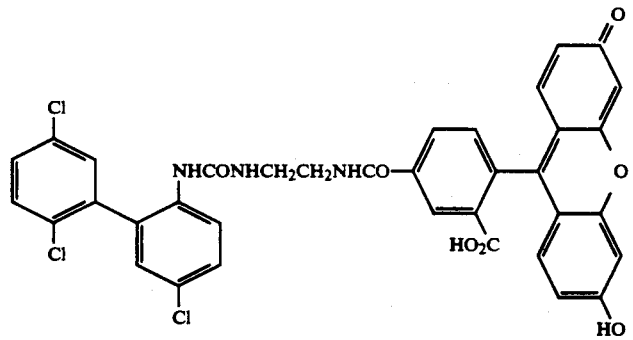

EXAMPLE 33

A tracer with the following structure was prepared from 2-Adipamido-2',4,4',5,5'-pentachlorobiphenyl (Example 8C) and 4'-aminomethyl fluorescein according to the method in Example 23A.

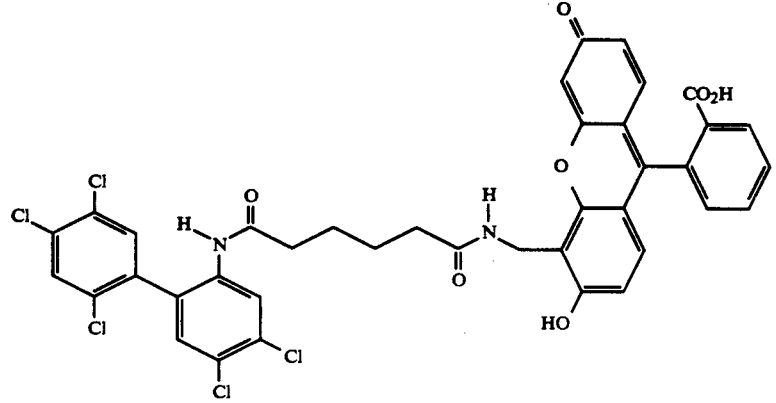

EXAMPLE 34

A tracer with the following structure was prepared from 2-Adipamido-2',4,4',5,5'-pentachlorobiphenyl (Example 8C) and 4'-(N-glycylaminomethyl)-fluorescein according to the method in Example 23A.

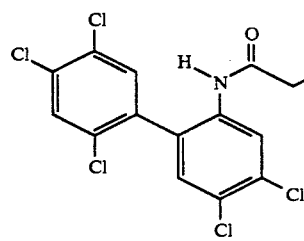
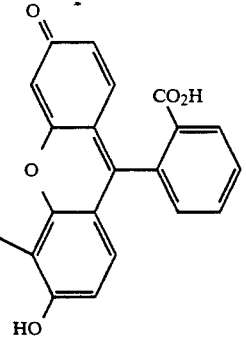

EXAMPLE 35

A tracer with the following structure was prepared from-Adipamido-2',4,4',5,5'-pentachlorobiphenyl (Example 8C) and 5-[N-(2-aminoethyl)carboxamido]-fluorescein according to the method in Example 23A.

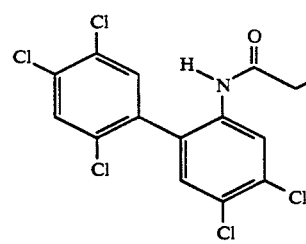

EXAMPLE 36

A tracer with the following structure was prepared from-Adipamido-2',4,4',5,5'-pentachlorobiphenyl (Example 8C) and 6-[N-(2-aminoethyl)carboxamido]-fluorescein according to the method in Example 23A.

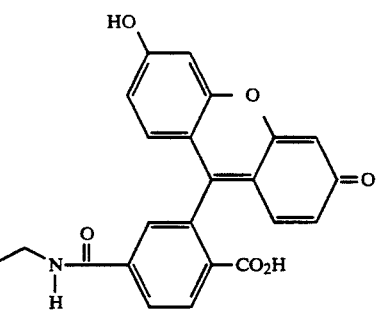

EXAMPLE 37

A tracer with the following structure was prepared from 2,4'-dichloro-4-adipamidobiphenyl (Example 9B) and 4'-aminomethyl fluorescein according to the method in Example 23A. Mass spectrum (FAB): m/z at 709 (M+1) for $C_{39}H_{30}Cl_2N_2O_7$.

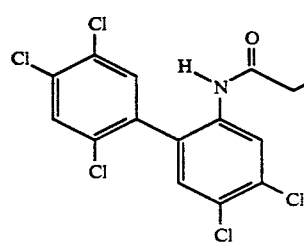
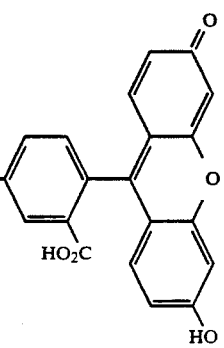

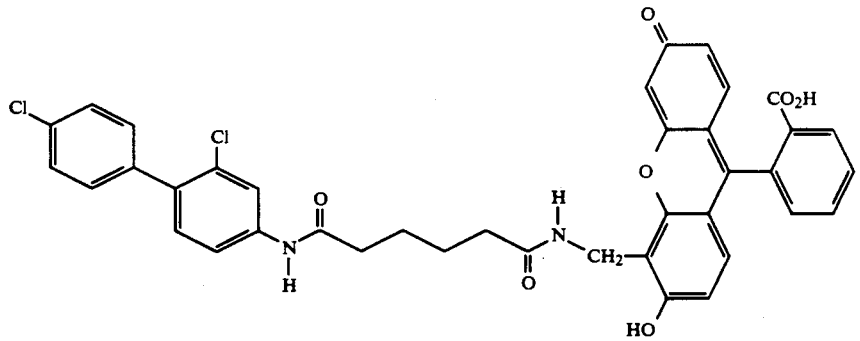

EXAMPLE 38

A tracer with the following structure was prepared from 2,4'-dichloro-4-adipamidobiphenyl (Example 9B) and 5-[N-(2-aminoethyl)carboxamido]-fluorescein according to the method in Example 23A. Mass spectrum (FAB): m/z at 766 (M+1) for $C_{41}H_{33}Cl_2N_3O_8$.

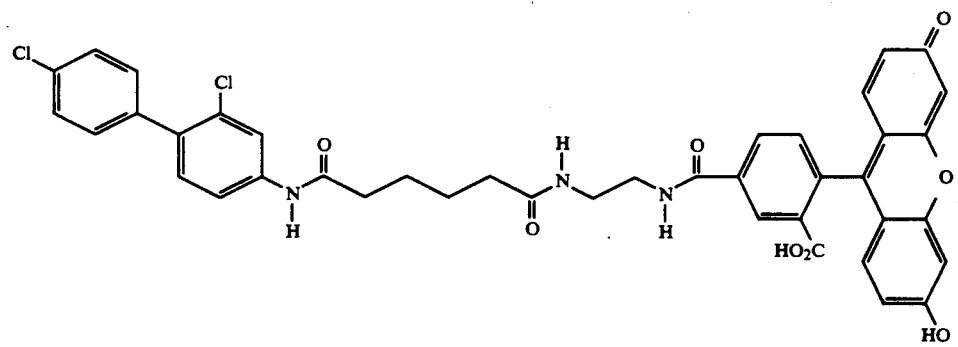

EXAMPLE 40

A tracer with the following structure was prepared from 2,4'-dichloro-4-adipamidobiphenyl (Example 9B) and 4'-(N-glycylaminomethyl)-fluorescein according to the method in Example 23A. Mass spectrum (FAB): m/z at 766 (M+1) for $C_{41}H_{33}Cl_2N_3O_8$.

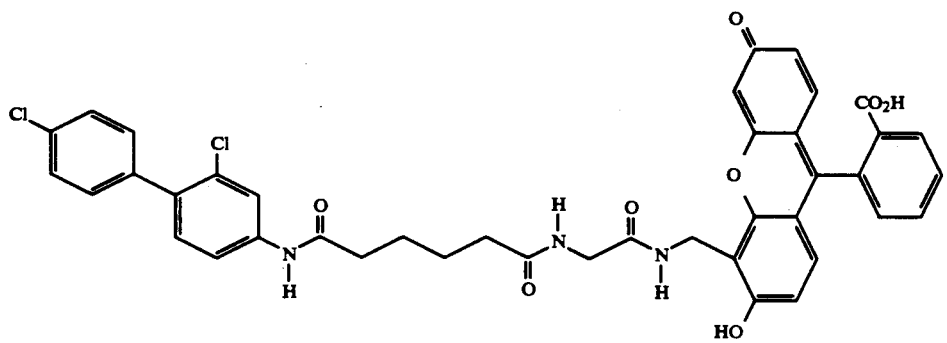

EXAMPLE 39

A tracer with the following structure was prepared from 2,4'-dichloro-4-adipamidobiphenyl (Example 9B) and 6-[N-(2aminoethyl)carboxamido]-fluorescein according to the method in Example 23A. Mass spectrum (FAB): m/z at 766 (M+1) for $C_{41}H_{33}Cl_2N_3O_8$.

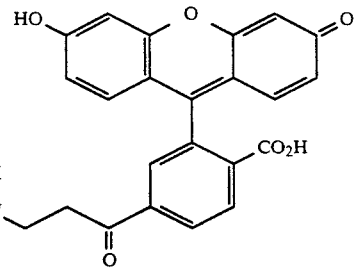

EXAMPLE 41

A tracer with the following structure was prepared

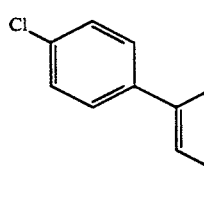

from 2,5,5'-trichloro-2'-adipamidobiphenyl (Example 10B) and 4'-aminomethyl fluorescein according to the method in Example 23A. Mass spectrum (FAB): m/z at 743 (M+1) for $C_{39}H_{29}Cl_3N_2O_7$.

EXAMPLE 42

A tracer with the following structure was prepared from 2,5,5'-trichloro-2'-adipamidobiphenyl (Example 10B) and 4'-(N-glycylaminomethyl)-fluorescein according to the method in Example 23A. Mass spectrum (FAB): m/z at 801 (M+1) for $C_{41}H_{33}Cl_3N_3O_8$.

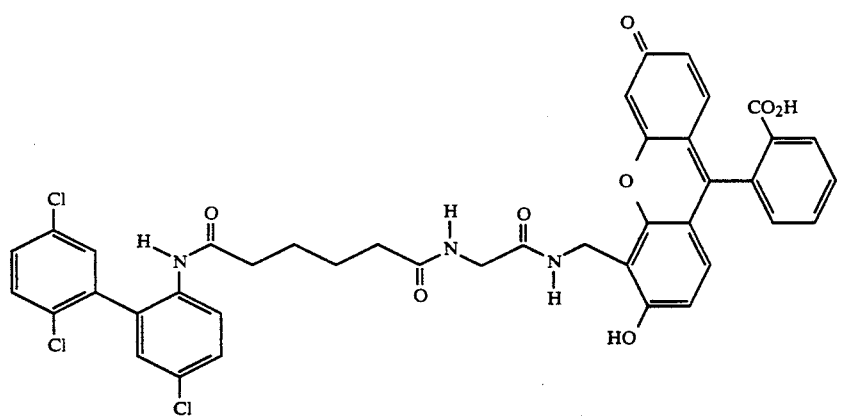

EXAMPLE 43

A tracer with the following structure was prepared from 2,5,5'-trichloro-2'-adipamidobiphenyl (Example 10B) and 5-[N-(2-aminoethyl)carboxamido]-fluorescein according to the method in Example 23A. Mass spectrum (FAB): m/z at 801 (M+1) for $C_{41}H_{33}Cl_3N_3O_8$.

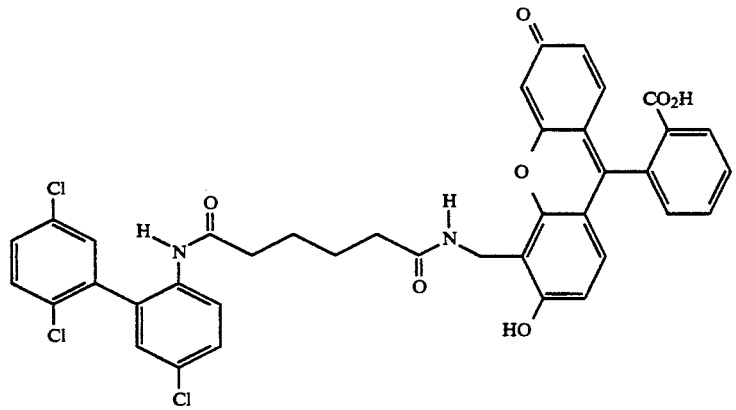

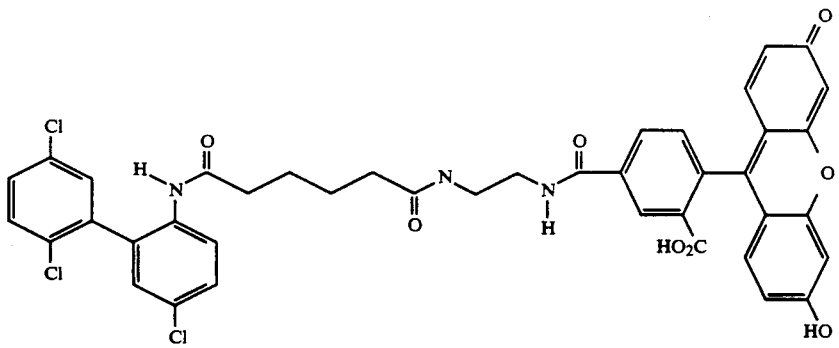

EXAMPLE 44

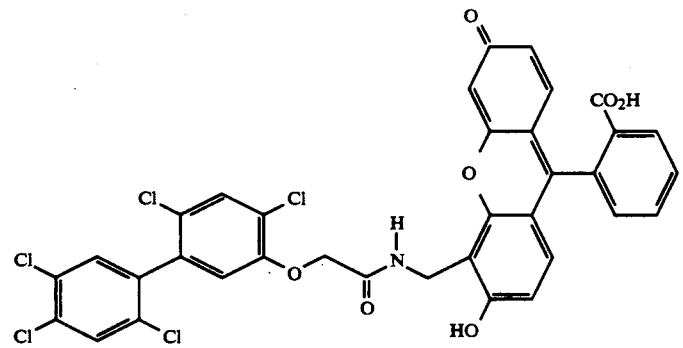

EXAMPLE 46

A tracer with the following structure was prepared from 2,5,5'-trichloro-2'-adipamidobiphenyl (Example 10B) and 6-[N-(2-aminoethyl)carboxamido]-fluorescein according to the method in Example 23A. Mass spectrum (FAB): m/z at 801 (M+1) for $C_{41}H_{33}Cl_3N_3O_8$.

chlorobiphenyl (Example 11B) and 4'-aminomethyl fluorescein according to the method in Example 23B.

EXAMPLE 46

A tracer with the following structure was prepared from 5-(Methoxycarboxylato)-2,2',4,4',5'-pentachlorobiphenyl (Example 11B) and 4'-(N-

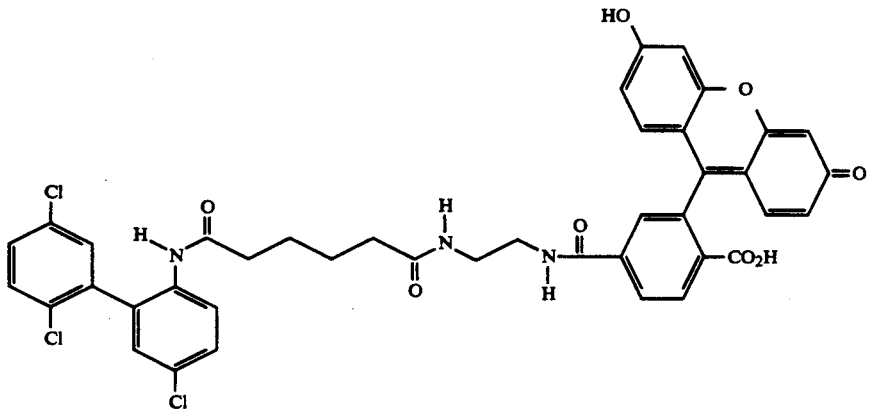

EXAMPLE 45

A tracer with the following structure was prepared from 5-(Methoxycarboxylato)-2,2',4,4',5'-pentachlorobiphenyl (Example 11B) and 4'-(N-glycylaminomethyl)fluorescein according to the method in Example 23B.

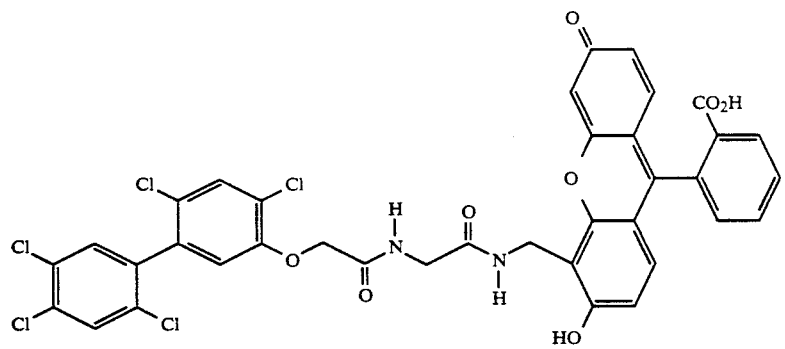

EXAMPLE 47

A tracer with the following structure was prepared from 5-(Methoxycarboxylato)-2,2',4,4',5'-pentachlorobiphenyl (Example 11B) and 6-[N-(2-aminoethyl)carboxamido]-fluorescein according to the method in Example 23B.

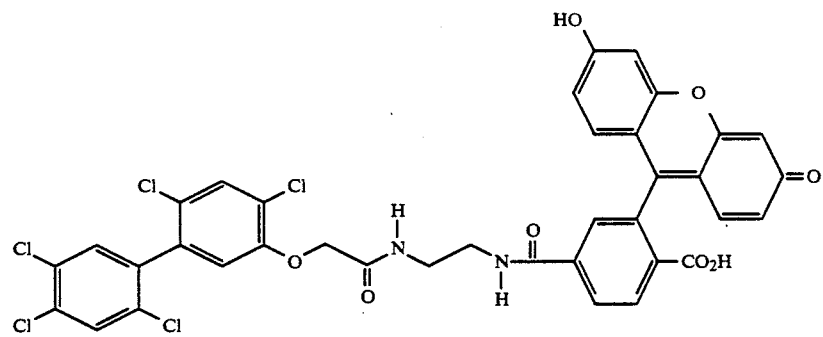

EXAMPLE 48

A tracer with the following structure was prepared from 5-(Methoxycarboxylato)-2,2',4,4',5'-pentachlorobiphenyl (Example 11B) and 5-[N-(2-aminoethyl)carboxamido]-fluorescein according to the method in Example 23B.

EXAMPLE 49

A tracer with the following structure was prepared form 5-(Methoxycarboxylato)-2,2',4,4',5'-penta-

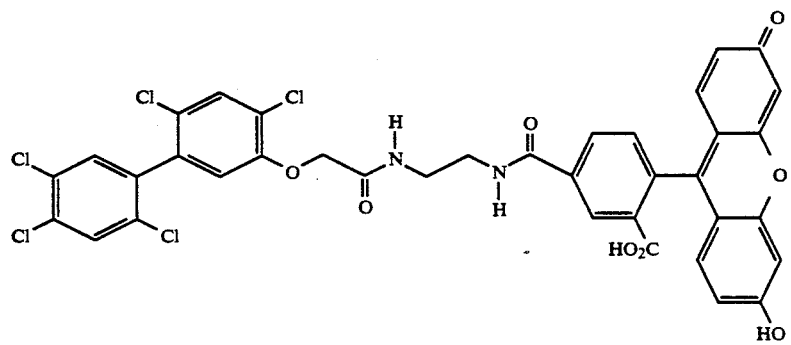

chlorobiphenyl (Example 11B) and 5-[N-(6-aminohexyl)carboxamido]-fluorescein according to the method in Example 23B.

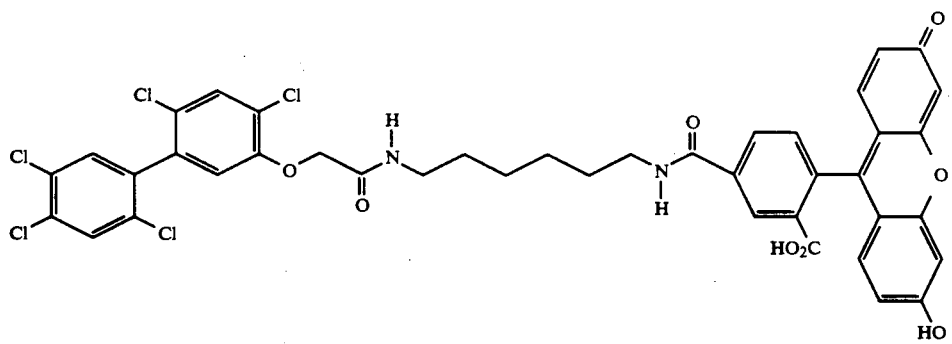

EXAMPLE 50

A tracer with the following structure was prepared from 5-(Methoxycarboxylato)-2,2',4,4',5'-pentachlorobiphenyl (Example 11B) and 5-aminomethyl fluorescein according to the method in Example 23B.

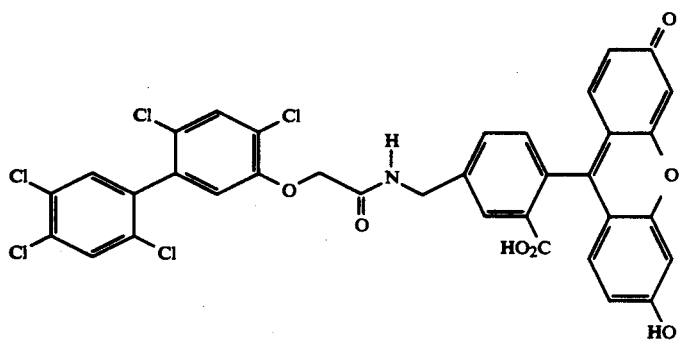

EXAMPLE 51

A tracer with the following structure was prepared from 4-(methoxycarboxylato)-2,2',4',5,5'-pentachlorobiphenyl (Example 12B) and 4'-aminomethyl fluorescein according to the method in Example 23B.

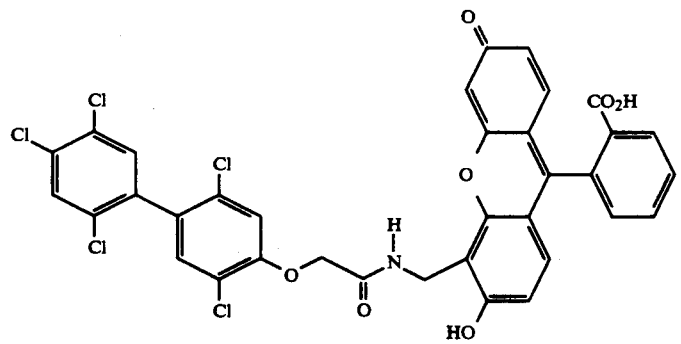

EXAMPLE 52

A tracer with the following structure was prepared from 4-(methoxycarboxylato)-2,2',4',5,5'-pentachlorobiphenyl (Example 12B) and 4'-(N-glycylaminomethyl)fluorescein according to the method in Example 23B.

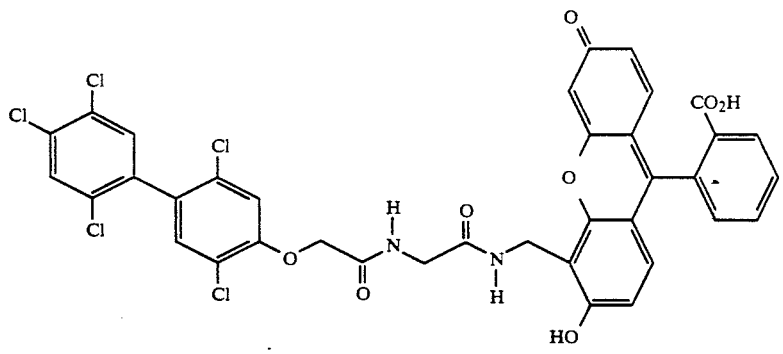

EXAMPLE 53

A tracer with the following structure was prepared from 4-(methoxycarboxylato)-2,2',4',5,5'-pentachlorobiphenyl (Example 12B) and 6-[N-(2-aminoethyl)carboxamido]-fluorescein according to the method in Example 23B.

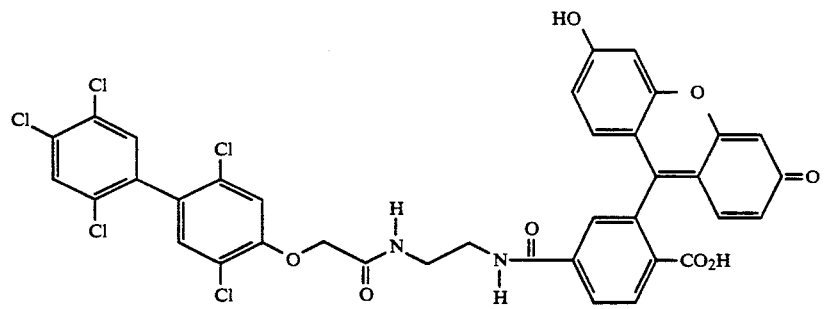

from 4-(methoxycarboxylato)-2,2',4',5,5'-pentachlorobiphenyl (Example 12B) and 5-[N-(2-aminoethyl)carboxamido]-fluorescein according to the method in Example 23B.

EXAMPLE 55

A tracer with the following structure was prepared from 4-(methoxycarboxylato)-2,2',4',5,5'-penta-

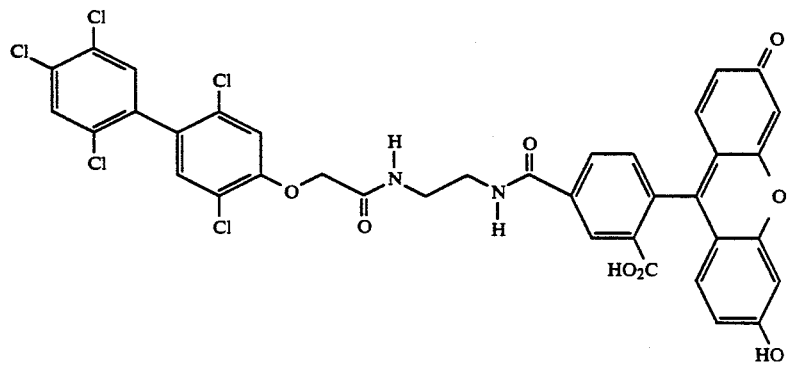

EXAMPLE 54

A tracer with the following structure was prepared from 4-(methoxycarboxylato)-2,2',4',5,5'-pentachlorobiphenyl (Example 12B) and 5-[N-(6-aminohexyl)carboxamido]-fluorescein according to the method in Example 23B.

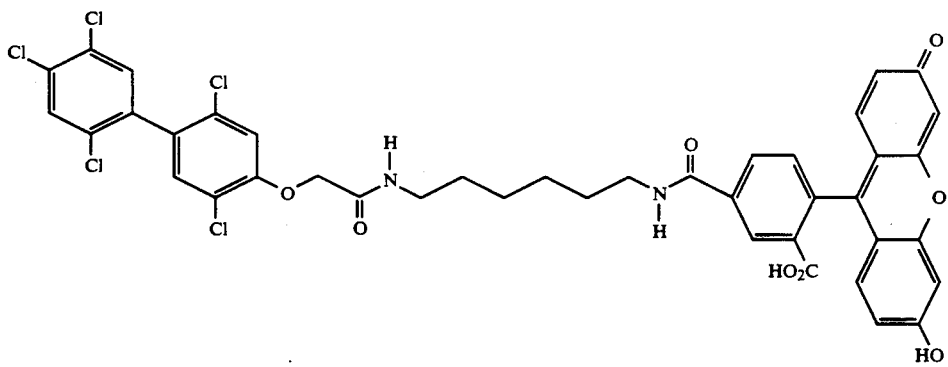

EXAMPLE 56

A tracer with the following structure was prepared from 4-(methoxycarboxylato)-2,2',4',5,5'-pentachlorobiphenyl (Example 12B) and 5-aminomethyl fluorescein according to the method in Example 23B.

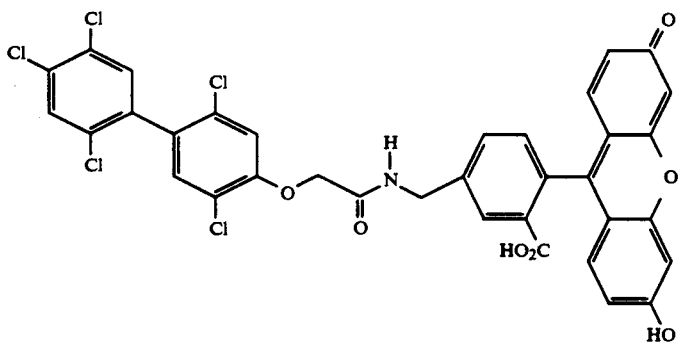

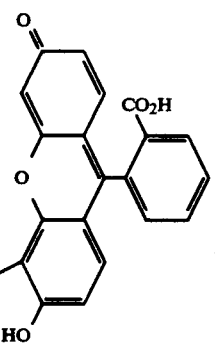

EXAMPLE 57

A tracer with the following structure was prepared from 2-(methoxycarboxylato)-2',4,4',5,5'-pentachlorobiphenyl (Example 13B) and 4'-aminomethyl fluorescein according to the method in Example 23B.

EXAMPLE 58

A tracer with the following structure was prepared from 2-(methoxycarboxylato)-2',4,4',5,5'-pentachlorobiphenyl (Example 13B) and 4'-(N-glycylaminomethyl)fluorescein according to the method in Example 23B.

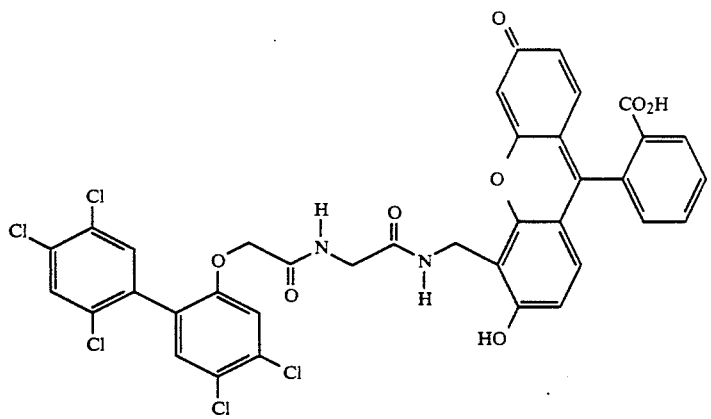

EXAMPLE 59

A tracer with the following structure was prepared from 2-(methoxycarboxylato)-2',4,4',5,5'-pentachlorobiphenyl (Example 13B) and 5-[N-(2-aminoethyl)carboxamido]-fluorescein according to the method in Example 23B.

chlorobiphenyl (Example 13B) and 6-[N-(2-aminoethyl)carboxamido]-fluorescein according to the method in Example 23B.

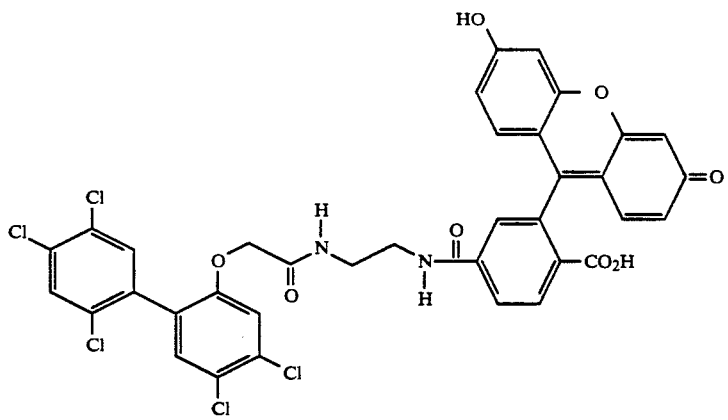

EXAMPLE 61

A tracer with the following structure was prepared from 2-(methoxycarboxylato)-2',4,4',5,5'-penta-

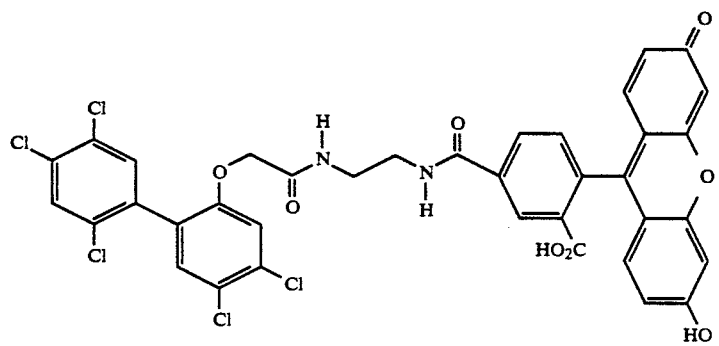

EXAMPLE 60

A tracer with the following structure was prepared from 2-(methoxycarboxylato)-2',4,4',5,5'-pentachlorobiphenyl (Example 13B) and 5-[N-(6-aminohexyl)carboxamido]-fluorescein according to the method in Example 23B.

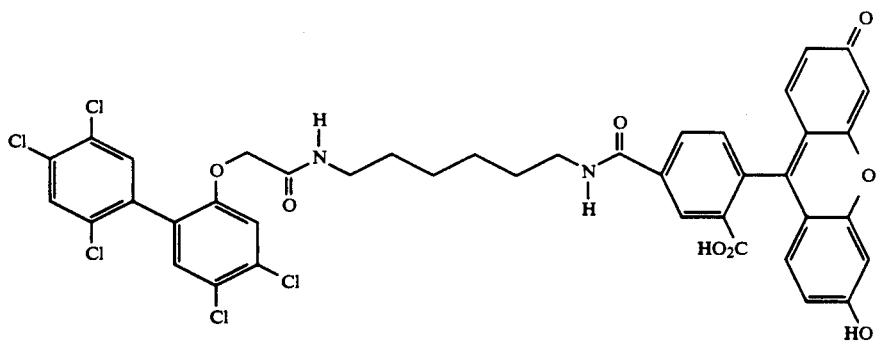

EXAMPLE 62

A tracer with the following structure was prepared from 2-(methoxycarboxylato)-2',4,4',5,5'-pentachlorobiphenyl (Example 13B) and 5-aminomethyl fluorescein according to the method in Example 23B.

EXAMPLE 63

A tracer with the following structure was prepared from 4-(Butoxy-4-carboxylato)-2-chlorobiphenyl (Example 14B) and 4'-aminomethyl fluorescein according to the method in Example 23A.

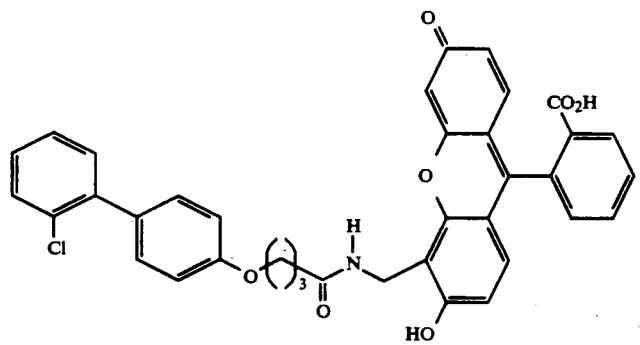

EXAMPLE 64

A tracer with the following structure was prepared from 4-(Butoxy-4-carboxylato)-2-chlorobiphenyl (Example 14B) and 4'-(N-glycylaminomethyl)-fluorescein according to the method in Example 23A.

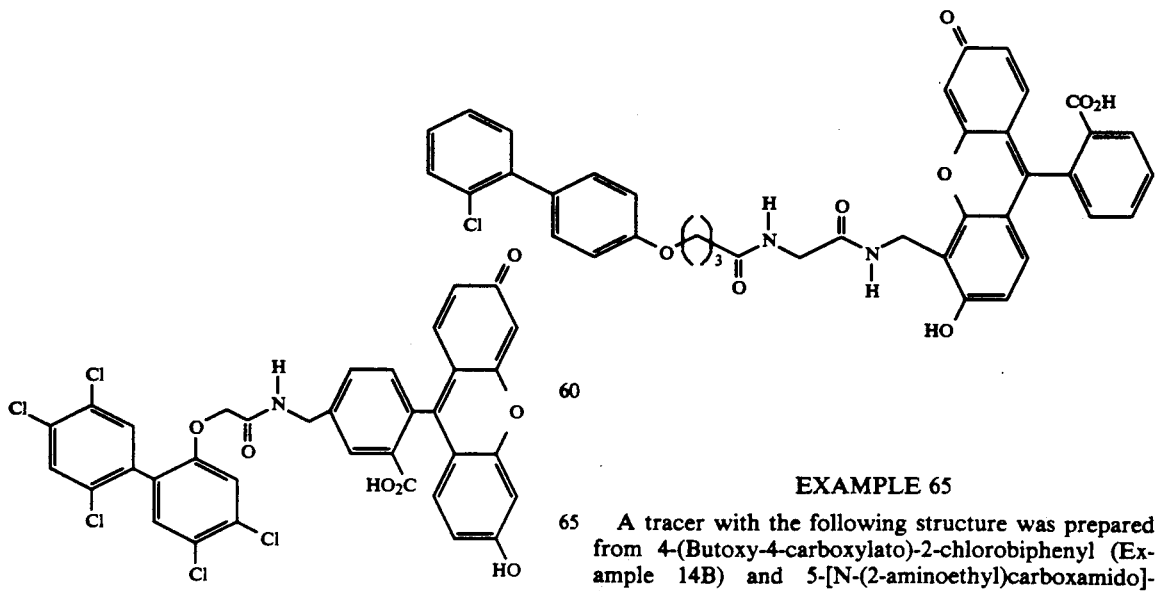

EXAMPLE 65

A tracer with the following structure was prepared from 4-(Butoxy-4-carboxylato)-2-chlorobiphenyl (Example 14B) and 5-[N-(2-aminoethyl)carboxamido]-fluorescein according to the method in Example 23A.

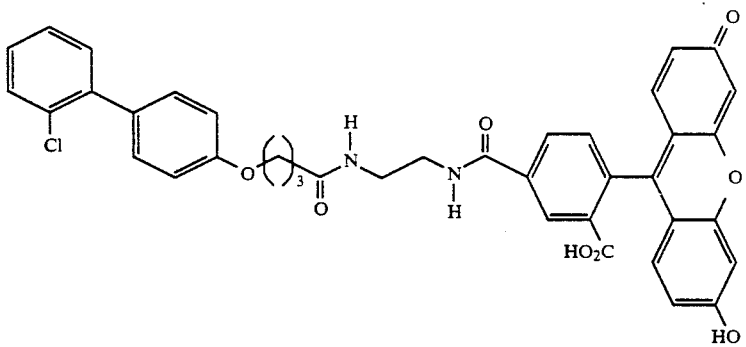

EXAMPLE 66

A tracer with the following structure was prepared from 4-(Butoxy-4-carboxylato)-2-chlorobiphenyl (Example 14B) and 6-[N-(2-aminoethyl)carboxamido]-fluorescein according to the method in Example 23A.

binding to tracers and displacement of the tracers from the antibody by PCBs in the $TD_x$ instrument. Antibodies with adequate net millipolarization and span were demonstrated in some bleeds at 6 weeks from initial inoculation.

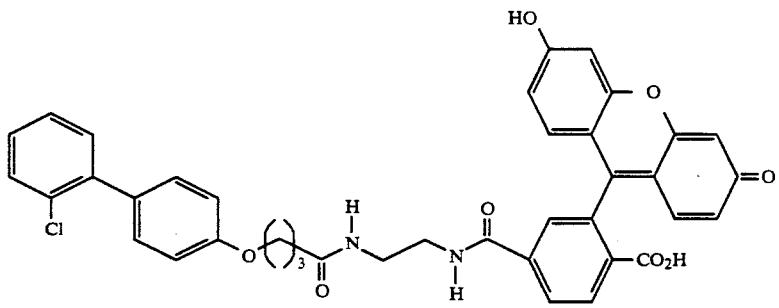

EXAMPLE 67

A tracer with the following structure was prepared from 4-(Butoxy-4-carboxylato)-2-chlorobiphenyl (Example 14B) and 5-aminomethyl fluorescein according to the method in Example 23A.

Production of Hybridomas

Four to six week old female BALB/c mice were injected subcutaneously at four weeks intervals with 0.2 mL of a mixture of each immunogen, (Example 16 and Example 17), suspended in mixture consisting of: 0.06 mL of immunogen, Example 16, at 5 mg/mL; 0.06 mL

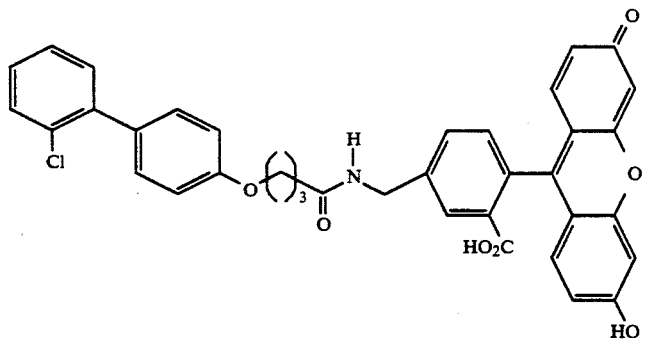

Production of Antisera

Example 68

Female New Zealand White (NZW) rabbits, approximately four to five months old, were injected subcutaneously and intramuscularly with an initial inoculation of 0.2 mg of the immunogen (Examples 16-22) in Freund's Complete Adjuvant followed by a day 14 boost of 0.1 mg of the immunogen, and thereafter monthly booster injections of 0.05 mg in Freund's Incomplete Adjuvant. Bleeds were taken two weeks following each booster injection and the serum tested for of immunogen, Example 17, at 5 mg/mL; 1.88 mL saline; and 100 μg of monophosphoryl lipid A and trehalose dimycloate adjuvant (Ribi Immunochem Research, Inc). Three months from initial inoculation, upon testing positive for antibody activity on the $TD_x$ instrument, the donor mice were killed by cervical dislocation three days following the last immunization; the spleen was removed aseptically and placed in a plastic Petri dish with 5 mL of cold Dulbecco's Minimal Essential Medium (DMEM), with 2.0 mM L-glutamine and 50 μg/mL Gentamycin (Medium A). The spleen was dissociated into a single cell suspension; the cells were centrifuged to a pellet and the red cells lysed by resuspension in 2 mL of 0.83% ammonium chloride in 10 mM Tris buffer. After letting stand for 2 min., 20–30 mL of fresh medium A was added. The cells were washed by centrifugation and resuspended in 10 mL of fresh medium A.

An immunoglobulin non-secreting mouse myeloma cell line (SP 2/0) deficient in the enzyme hypoxanthine-guanine phosphoribosyl transferase (HGPRT-, EC2.4.2.8), as disclosed by Kearney, *Journal of Immunology*, 1979,123,1548, which is incorporated herein by reference, was used as the fusion partner. The myeloma cell line was maintained in medium A with 20% fetal calf serum added. For three days prior to fusion, 0.1 mM 8-azaguanine was added to the myeloma cells in order to kill any HGPRT+revertants. On the day of fusion, the myeloma cells were harvested, washed once in medium A, and resuspended in 5 mL medium A. The myeloma and previously harvested spleen cells were counted using a hemacytometer and their viability assessed by Erythrosin B stain exclusion.

The fusion technique used was modified from that of Gefter et. al.,*Somatic Cell Genetics*, 1977, 3, 231, which is hereby incorporated by reference. Described below is the fusion experiment which yielded the hybridoma designated as H51C129. This hybridoma is deposited at the American Type Culture Collection (A.T.C.C.), 12301 Parklawn Drive, Rockville, MD, and is designated as A.T.C.C. Deposit No. HB 10538.

To a sterile 50 mL conical centrifuge tube was added $1-1.5 \times 10^8$ spleen cells with an equal number of SP 2/0 myeloma cells. The myeloma-spleen cell suspension was centrifuged at 1400 rpm for 5 minutes to pellet the cells together. The supernatant was aspirated off and the tube tapped gently to loosen the cell pellet and 1 mL of 50% polyethylene glycol (PEG, MW 1000, Sigma) in DMEM, without serum, was added to the cell pellet. The cells were resuspended gently in PEG solution over a period of 1 minute by slowly aspirating up and down using a 1 mL pipette. The tube was held in the hand for an additional 1 minute and then 1 mL of medium A was added slowly to dilute the PEG. The cells are allowed to stand for an additional 1 minute without agitation or mixing. An additional 20 mL of medium A was added over a period of 3 to 5 minutes, and the cells pelleted at 1400 rpm for 5 minutes. The supernatant was aspirated off and the cells resuspended in 20 mL of medium A with 20% fetal calf serum, $1 \times 10^{-4}$M hypoxanthine, $4 \times 10^{-7}$M aminopterin and $3 \times 10^{-6}$M thymidine (medium C or HAT selective medium).

Example 69

Selection of Hybridomas Producing Monoclonal Antibodies to PCB Immunogen of Example 17

The cell suspension from example 1 above was transferred into a 75 cm$^2$ T-flask and incubated at 37° C. in a 5% CO$_2$ incubator for 1–3 hours. The cell suspension was then diluted to $1 \times 10^6$ spleen cells/mL with medium C, and 1 mL volumes of the cell suspensions were added to each well of a 24-well Costar plates. These plates were incubated for 24 hours at 37° C. and 5% CO$_2$. After the incubation period 1 mL volumes of feeder cell (non-immunized BALB/c mouse spleen cells) suspension in medium C at $2-3 \times 10^5$ cells/mL was added to each of the 24 wells of the Costar plates and incubated at 37° C., 5% CO$_2$ for 14–17 days. During this period, on alternate days, 1 mL volumes of medium is removed from each well by aspiration and replaced with 1 mL of fresh medium C. On day 10 the supernatants from the hybridoma containing wells were tested for antibody activity in the TDx instrument using selected tracers of Example 26 and Example 29, fenclofenac at 10% solution and 25 µL of hybridoma supernatant. Five hybridoma suspensions were chosen for further cloning by picking those supernatants with tracer binding in mP units greater than 20% over background. The cells from wells chosen for containing antibody activity were cloned by limiting dilution within 24 hours of sampling.

Example 70

Cloning of Hybridoma Culture that Produces Monoclonal Antibodies to PCBs

The cells in antibody secreting wells were diluted in a volume of medium B by a limiting dilution method to a concentration of 10 cells/mL. 100 µL of each diluted cell suspension were aliquoted into the wells of three 96-well Costar plates. 100 µL volumes of feeder cells in medium B at $5 \times 10^5$ cells/mL were added to each well and the plates incubated at 37° C., 5% CO$_2$ for 14 days. Supernatants were again tested for antibody activity using the same protocol as in Example 69. The antibody producing clones were then expanded without feeder cells in 24 well Costar plates and finally in 25 cm$^2$ T-flasks. $32 \times 10^6$ cells/mL samples of the clone were then stored in medium B with 10% glycerol added, in liquid nitrogen. 1–2 mL samples were then further evaluated for displacement on the TD$_x$ instrument protocol and one clone (H51C129) was selected for ascites production.

Example 71

In Vivo Production of Monoclonal Antibodies to Example 70

An in vivo method for obtaining large amounts of monoclonal antibodies involved the adaptation of Example 70 (hybridoma H51C129) to grow as an "ascites" tumor. Female BALB/c mice were primed by intraperitoneal injection of 0.5 mL of pristane (2,6,10,14-tetramethylpentadecane). Approximately 4–5 weeks following the pristane injection, aliquots containing $1.5 \times 10^6$ actively growing hybridoma cells harvested from in vitro cultures as described in Example 69 were innoculated into the peritoneal cavities of primed mice. Seven days following hybridoma cell injection, 5–10 mL of ascites fluid was harvested from each mouse. Upon purification by ammonium sulfate precipitation, approximately 24.6 mg of antibody was obtained per mL of ascites fluid.

Example 72

PCB Fluorescence Polarization Immunoassays

As described previously, the reagents for the FPIA of the present invention comprise tracers and antibodies raised against immunogens of the present invention, specific for PCBs. In addition, conventionally used assay solutions including a dilution buffer, and PCBs calibrators and controls are prepared. The preferred procedure was designed to be used in conjunction with an automated instrument such as Abbott Laboratories' TD$_x$, AD$_x$, or IM$_x$ systems; however, manual assays can also be performed. In both procedures, the test sample can be mixed with a pretreatment solution and antibody in dilution buffer before a background reading is taken. The tracer is then added to the test solution. After incubation, a fluorescence polarization reading is taken.

The following extraction protocol was used to extract the non-polar PCBs into a water miscible solvent that could then be used in the automated assay on the $TD_x$ instrument. 1 mL of standard or test sample was added to 9 mL of 10% acetone/hexane; mixed vigorously for one minute; sonicated in a water bath for 10 min. and centrifuged for 10 min at 1500 G. Then, 6 mL of hexane/acetone was removed and added to a 0.5 mL bed of propylene glycol. Hexane/acetone was evaporated off at 60° C. for 15 minutes under a gentle stream of air. After vigorous mixing, the mixture was sonicated for 10 minutes and centrifuged for 10 minutes at 1500 G. Following this, 0.5 mL $TD_x$ buffer was added to the mixture; mixed vigorously; sonicated 10 minutes and centrifuged for 5 minutes at 10 k/G. The solution from step 3 above was added to a sample well of a $TD_x$ instrument and run via an automated assay protocol.

In the automated assays, the fluorescence polarization value of each calibrator, control or test sample was determined and printed on the output tape of the $TD_x$, $AD_x$ or $IM_x$ instrument. The instrument also generated a standard curve by plotting the polarization of each calibrator versus its concentration, using a nonlinear regression analysis. The concentration of each control or sample was read off the stored curve and printed on the output tape.

The following reagents were used in the preferred automated PCB assays; one assay consisted of an antibody and tracer combination to bind and displace aroclors with a high concentration of highly chlorinated biphenyls, such as aroclors 1260 and 1254; another assay consisted of an antibody and tracer combination to bind and displace aroclors with a high concentration of comparably lower chlorinated biphenyls, such as aroclors 1016, 1221, 1232, 1242 and 1248:

1) the pretreatment solution comprising 10% fenclofenac in 30 mM NaOH in water;
2) the respective assay's tracers diluted in 50% methanol in potassium phosphate buffer (0.15M phosphate buffer, pH 7.5).
3) the respective assay's antibody comprising rabbit antisera or mouse monoclonal antibody raised against a PCB immunogen, diluted in $TD_x$ buffer (0.1M phosphate buffer, pH 7.5, containing 0.01% bovine gamma globulin and 0.1% sodium azide) with 30% glycerol;
4) a diluent buffer comprising $TD_x$ buffer;
5) two sets of calibrators comprising 10% acetone in hexane containing 0.00, 1.0, 5.0, 15, 30, and 60 µg/mL of PCB aroclors 1221 and 1260;
6) controls comprising 5 µg/mL of aroclors 1221, 1254 and 1260.

All polarized fluorescent measurements were made using the $TD_x$ instrument which performed the assay in accordance with the following protocol:

1) 22.5 µL of standard or test sample, and 12.5 µL each of the antibody reagent and the pretreatment reagent were delivered into a cuvette. A sufficient volume of diluent buffer was added to raise the volume to 1 mL, and a background intensity reading was taken;
2) 12.5 µL each of pretreatment reagent and antibody, 25 µL of the tracer, and the second 22.5 µL of sample and were added to the cuvette, and a sufficient volume of diluent buffer was added to raise the volume to 2.0 mL;
3) the reaction mixture was incubated;
4) the fluorescence polarization due to tracer binding to the antibody was obtained by subtracting the polarized fluorescence intensities of the background from the final polarized fluorescence intensities of the mixture; and
5) the polarization value for the unknown test sample was compared to a standard curve prepared using calibrators of known PCB content.

Example 73

FPIA

Data obtained from an immunoassay according to the present invention are summarized herein. The binding of tracer to antibody and the displacement of the tracer by the PCB present in the sample are summarized in Table 1 below. Various combinations of antibodies developed in response to immunogens and tracers, as described in the Examples above, were tested. In each combination where the tracer bound to the antibody, the net polarization was at least 150 millipolarization units, the 5 µg/mL span was at least 15 millipolarization units, and the intensity ratio varied between three and ten times that of the background noise.

As the data from Table 1 exemplify, the combination of the antibody produced by the immunogen of Example 16 and the tracer of Example 26 provided good binding to the antibody and good displacement by PCB aroclors 1260 and 1254. The combination of the polyclonal or monoclonal antibody produced by the immunogen of Example 17 and the tracer of Example 29 provided good binding to the antibody and good displacement by PCB aroclors 1016, 1221, 1232, 1242, 1248 and 1254.

TABLE 1
(net mP)

| Immunogen Example # | Tracer Example # RABBIT #(dil) | 24 | 25 | 26 | 27 | 28 | 29 | 30 | 31 | 32 | 37 | 38 | 39 | 40 | 41 | 42 | 43 | 44 |
|---|---|---|---|---|---|---|---|---|---|---|---|---|---|---|---|---|---|---|
| | Normal rabbit(1:1800) | 100 | 103 | 105 | 74 | 72 | 79 | | 43 | 43 | 61 | 70 | 42 | 51 | 41 | 32 | 56 | 57 |
| 18 | 4757(1:1800) | 74 | 84 | 129 | 71 | 72 | 75 | | — | 319 | 47 | 60 | 48 | 64 | 224 | 249 | 214 | 235 |
| 18 | 4758(1:1800) | 80 | 134 | 279 | 65 | 69 | 76 | | 207 | 324 | 55 | 62 | 44 | 56 | 278 | 238 | 246 | 269 |
| 18 | 4760(1:1800) | 95 | 217 | 275 | 77 | 75 | 87 | | 302 | 289 | 65 | 68 | 57 | 65 | 265 | 247 | — | 246 |
| 16 | 5272(1:1800) | 129 | 200 | 314 | 75 | 58 | 82 | | — | 334 | 54 | 50 | 46 | 56 | 215 | 197 | 195 | 208 |
| 16 | 5273(1:1800) | 157 | 241 | 259 | 76 | 70 | 84 | | — | 231 | 47 | 59 | 48 | 53 | 202 | 150 | — | 165 |
| 16 | 5274(1:1800) | 247 | 287 | 239 | 73 | 69 | 75 | | — | 170 | 39 | 59 | 43 | 53 | 245 | 198 | — | 216 |
| 17 | 5360(1:1800) | 101 | 116 | 114 | 297 | 207 | 239 | | — | 44 | 258 | 164 | 242 | 216 | 34 | 32 | 42 | 55 |
| 17 | 5361(1:1800) | 99 | 112 | 109 | 294 | 224 | 243 | | — | 43 | 261 | 170 | 257 | 228 | 36 | 32 | 44 | 53 |
| 17 | 5362(1:1800) | 106 | 124 | 120 | 290 | 182 | 204 | | — | 64 | 258 | 179 | 222 | 205 | 47 | 44 | 53 | 64 |

| Immunogen Example # | Tracer Example # | 45 | 46 | 47 | 48 | 49 | 50 | 51 | 52 | 53 | 54 | 55 | 56 | 57 | 58 | 59 | 60 | 61 | 62 |
|---|---|---|---|---|---|---|---|---|---|---|---|---|---|---|---|---|---|---|---|
| | Normal rabbit(1:200) | 78 | 94 | 71 | 40 | 115 | 87 | 117 | 98 | 53 | 36 | 79 | 141 | | | | | | |
| 18 | 4757(1:200) | 89 | 106 | 79 | 50 | 122 | 93 | 128 | 112 | 63 | 40 | 114 | 50 | | | | | | |
| 18 | 4758(1:200) | 78 | 105 | 95 | 61 | 127 | 126 | 123 | 112 | 58 | 46 | 122 | 162 | | | | | | |
| 18 | 4760(1:200) | 92 | 97 | 84 | 42 | 124 | 102 | 122 | 118 | 73 | 44 | 117 | 207 | | | | | | |
| 16 | 5272(1:200) | 90 | 109 | 178 | 47 | 136 | 108 | 135 | 216 | 168 | 86 | 136 | — | | | | | | |
| 16 | 5273(1:200) | 90 | 109 | 94 | 43 | 138 | 105 | 121 | 133 | 118 | 60 | 123 | 196 | | | | | | |
| 16 | 5274(1:200) | 102 | 118 | 95 | 45 | 129 | 111 | 126 | 136 | 77 | 37 | 119 | 172 | | | | | | |
| 17 | 5360(1:200) | 96 | 104 | 88 | 43 | 132 | 106 | 149 | 124 | 80 | 50 | 126 | 184 | | | | | | |
| 17 | 5361(1:200) | 86 | 114 | 83 | 42 | 128 | 106 | 153 | 175 | 92 | 56 | 131 | 193 | | | | | | |
| 17 | 5363(1:200) | — | 132 | 141 | 71 | 144 | 132 | 138 | 133 | 80 | 50 | 131 | 185 | | | | | | |

| Immunogen Example # | Tracer Example # | 45 | 46 | 47 | 48 | 49 | 50 | 51 | 52 | 53 | 54 | 55 | 56 | 57 | 58 | 59 | 60 | 61 | 62 |
|---|---|---|---|---|---|---|---|---|---|---|---|---|---|---|---|---|---|---|---|
| 21 | 6033(1:1400) | | | | 216 | 176 | 240 | | | | | | | 24 | 180 | 144 | 77 | 196 | 268 |
| 21 | 6034(1:1400) | | | | 221 | 151 | 216 | | | | | | | 23 | 182 | 160 | 82 | 175 | 287 |
| 21 | 6035(1:1400) | | | | 212 | 150 | 233 | | | | | | | 24 | 102 | 133 | 40 | 174 | 212 |
| 20 | 6036(1:1400) | | | | | | | 224 | 184 | 26 | 181 | 161 | 231 | | | | | | |
| 20 | 6037(1:1400) | | | | | | | 214 | 164 | 28 | 122 | 158 | 198 | | | | | | |
| 20 | 6038(1:1400) | | | | | | | 205 | 155 | 27 | 113 | 158 | 217 | | | | | | |
| 19 | 6039(1:1400) | 187 | 185 | 231 | | | | | | | | | | | | | | | |
| 19 | 6044(1:1400) | 192 | 177 | 228 | | | | | | | | | | | | | | | |
| 19 | 6046(1:1400) | 202 | 178 | 223 | | | | | | | | | | | | | | | |

TABLE 2

| | 5 μg/mL Spans | | |
|---|---|---|---|
| Immunogen: | EXAMPLE 17 | EXAMPLE 17 | EXAMPLE 16 |
| Antisera: | monoclonal | polyclonal | polyclonal |
| Tracer: | EXAMPLE 29 | EXAMPLE 29 | EXAMPLE 26 |

| Aroclor | mP | span | mP | span | mP | span |
|---|---|---|---|---|---|---|
| 0 control | 218 | — | 192 | — | 216 | — |
| 1260 | 217 | 1 | 178 | 14 | 175 | 41 |
| 1254 | 176 | 42 | 112 | 80 | 137 | 79 |
| 1248 | 157 | 61 | 111 | 81 | 194 | 22 |
| 1242 | 149 | 69 | 96 | 96 | 199 | 17 |
| 1232 | 161 | 57 | 92 | 100 | 203 | 13 |
| 1221 | 165 | 53 | 109 | 83 | 212 | 4 |
| 1016 | 142 | 76 | 92 | 100 | 208 | 8 |

For each assay system, the binding of tracer to antibody and displacement of tracer by each aroclor mixture in the sample are summarized in Table 2 above.

Example 74

The cross-reactivity of a variety of structurally similar compounds was tested, and is as summarized in Table 3 below. Compounds were assayed by adding a known quantity of the test compound to PCB free prolpylene glycol, diluting to 50% solution in TDx buffer, and assaying the test samples on the $TD_x$ instrument. The compounds were tested at a concentration of 100 μg/mL. The antisera or monoclonal antibody produced to the immunogens of the present invention, was determined to be highly specific to PCBs containing aroclors which in combination with the tracers of the present invention provide a sensitive FPIA for PCBs and is demonstrated by the data of Table 3.

TABLE 3

| | FPIA Specificity* | | |
|---|---|---|---|
| Immunogen: | EXAMPLE 16 | EXAMPLE 17 | |
| Antisera: | polyclonal | polyclonal | monoclonal |
| Tracer: | EXAMPLE 26 | EXAMPLE 29 | EXAMPLE 29 |
| Test Compound | | | |
| β-BHC | 0.0 | 0.018 | 0.0 |
| α-BHC | 0.0 | 0.0 | 0.0 |
| γ-BHC | 0.0 | 0.0 | 0.0 |
| δ-BHC | 0.0 | 0.0 | 0.0 |
| toxaphene | 0.0 | 0.0 | 0.0 |
| endosulfan I | 0.0 | 0.014 | 0.0 |
| endosulfan II | 0.0 | 0.0 | 0.0 |
| endrin | 0.013 | 0.0 | 0.0 |
| endosulfan sulfate | 0.0 | 0.0 | 0.0 |
| heptachlor | 0.0 | 0.0 | 0.0 |
| heptachlor epoxide | 0.0 | 0.0 | 0.0 |
| dieldrin | 0.0 | 0.0 | 0.0 |
| 4,4'-DDE | 0.0 | 0.0 | 0.0 |
| 4,4'-DDD | 0.0 | 0.0 | 0.0 |
| 1,2,4-trichlorobenzene | 0.15 | 0.023 | 0.8 |
| 1,2 dichlorobenzene | 0.0 | 0.0 | 0.0 |
| chlorobenzene | 0.0 | 0.0 | 0.0 |
| 2,5 dichlorophenol | 0.0 | 0.0 | 0.0 |
| 3,4 dichlorophenol | 0.0 | 0.0 | 0.0 |
| pentachlorophenol | 0.0 | 0.0 | 0.0 |
| 2,4 dichlorophenol | 0.0 | 0.0 | 0.0 |
| biphenyl | 0.0 | 0.0 | 0.0 |
| chlordane | 0.018 | 0.0 | 0.15 |
| 4,4'-DDT | 0.0 | 0.0 | 0.0 |
| Example 12B | — | — | 3.58 |
| Example 11B | — | — | 0.0 |
| Example 13B | — | — | 0.0 |

*units = μg/mL

Example 75

Fenclofenac was utilized in the assay system. The addition of fenclofenac to the assay minimizes the effect of any non-specific binding of the PCB and PCB tracers to serum proteins present in the assay system such as are found in the dilution buffer, antibody reagent or from the test sample. The final concentration of fenclofenac can range from about 0.005% to about 0.26%, preferably from about 0.02% to about 0.25%, with a concentration of about 0.13% being most preferred.

An experiment was conducted wherein fenclofenac was added to the sample pretreatment reagent used. Fenclofenac was added at concentrations of 0%, 2% and 10% solutions and tested against tracer Examples 28, 29, 31, and 32 in combination with normal rabbit serum which had not been innoculated with PCB immunogens and antisera Example 68 (immunogens from Examples 16, 17, and 18.) As the data of Table 4 exemplify, the addition of fenclofenac allowed specific antibody binding providing for acceptable net millipolarization and span.

TABLE 4

| Tracers: (units = mP) | EXAMPLE 28 | EXAMPLE 29 | EXAMPLE 31 | EXAMPLE 32 |
|---|---|---|---|---|
| | (without fenclofenac) | | (without fenclofenac) | |
| Normal Rabbit Serum 1:4 | >300 | >300 | >300 | >300 |
| | 2% fenclofenac | | 10% fenclofenac | |
| TDx Buffer | 28 | 42 | 23 | 26 |
| Normal Rabbit Serum 1:4 Antisera (polyclonal) 1:4 (Example 68) | 49 | 60 | 37 | 46 |
| Example 18      4757 | 53 | 65 | 87 | 327 |

TABLE 4-continued

| Tracers: (units = mP) | | EXAMPLE 28 | EXAMPLE 29 | EXAMPLE 31 | EXAMPLE 32 |
|---|---|---|---|---|---|
| (immunogen) | 4758 | 52 | 65 | 196 | — |
| | 4760 | 55 | 72 | 293 | 298 |
| Example 16 | 5360 | 228 | 276 | 50 | 52 |
| (immunogen) | 5361 | 265 | 276 | 47 | 52 |
| | 5362 | 256 | 266 | 50 | 51 |
| Example 17 | 5272 | 55 | 69 | 100 | 340 |
| (immunogen) | 5273 | 53 | 65 | 55 | 58 |
| | 5274 | 51 | 63 | 88 | 190 |

Example 76

Optionally, a PCB assay can be configured which utilizes a mixture of antibodies of Example 16 and Example 17, in combination with a mixture of tracers of Example 29 and Example 26 to assay all PCB aroclor mixtures in a single assay. The concentration ratios of the mixtures of antibodies and combined with mixtures of tracers can range from 10% to 90% of one antibody or tracer mixed with the other antibody or tracer type, with a mixture concentration ratio of about 3.5 parts antibody Example 16 mixed with 1 part of antibody Example 17, and 3.5 parts tracer Example 26 mixed with 1 part of tracer Example 29 being most preferred.

An experiment was conducted wherein 5 µg/mL of aroclor mixtures for 1260, 1254 1248, 1242, 1232, 1221 and 1016 were assayed in the preferred one assay, mixed reagent system. As summarized in Table 5, the mixed reagent system provided an assay with an acceptable net millipolarization value and span.

TABLE 5

| | Mixed Reagent Assay | |
|---|---|---|
| aroclor | mP | span |
| 0 | 227 | — |
| 1260 | 209 | 19 |
| 1254 | 207 | 21 |
| 1248 | 208 | 20 |
| 1242 | 207 | 21 |
| 1232 | 207 | 21 |
| 1221 | 210 | 18 |
| 1016 | 211 | 17 |

The incubation time for the assay can range from about 5 seconds to about 30 minutes. Preferably, the incubation time will be about less than five minutes. The incubation temperature also can vary between approximately ambient room temperature (25° C.) and approximately 42° C.; the preferred temperature is approximately 37° C. Incubation conditions and times can be varied by the routineer.

It will appreciated by those skilled in the art that many of the concepts of the present invention are equally applicable to other types of binding assays. The embodiments described and presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

What is claimed is:

1. A method for detecting the presence or amount of an analyte comprising polychlorinated biphenyl in a test sample, which method comprises the steps of:
(a) adding a known concentration of a tracer labeled with a detectable moiety and a known concentration of an analyte-specific antibody to the test sample to form a mixture, wherein the tracer has the general structure of

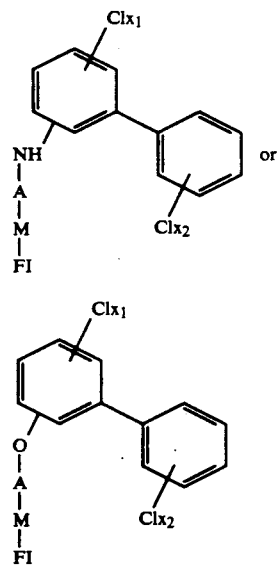

wherein
A is a spacer group consisting of from 0 to 50 carbon atoms and heteroatoms, including not more than ten heteroatoms, arranged in a straight or branched chain, saturated or unsaturated, wherein
(i) not more than two heteroatoms are linked in the sequence —NH—A—M—Fl or —O—A—M—Fl,
(ii) A is not a single heteroatom, and
(iii) branching occurs only on carbon atoms;
M is a linking group selected from the group consisting of

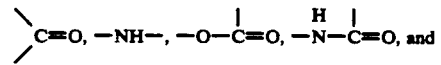

$$-\overset{H}{\underset{}{N}}-\overset{|}{C}=S.$$

Fl is a detectable moiety; and wherein independently $x_1=0-4$ and $x_2=0-5$, with the proviso that together $x_1$ and $x_2 \geq 1$;
(b) incubating said mixture for a time and under conditions sufficient to form labeled tracer-antibody and analyte-antibody complexes; and
(c) determining the presence or amount of tracer-antibody complexesformed as a measure of the presence or amount of analyte in the test sample.

2. The method according to claim 1 wherein said polychlorinated biphenyls comprise the following structure

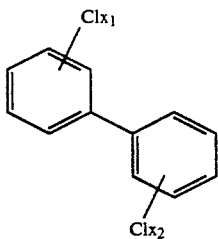

wherein independently $x_1=0-5$ and $x_2=0-5$, with the proviso that together $x_1$ and $x_2 > 1 [x=0-5]$.

3. The method according to claim 1 wherein said test sample is prepared by performing an extraction procedure prior to step (a).

4. The method according to claim 1 wherein the detectable moiety is selected from the group consisting of fluorescein and fluorescein derivatives.

5. The method according to claim 4 wherein said fluorescein derivatives are selected from the group consisting of fluorescein amine, carboxyfluorescein, α-iodoacetamidofluorescein, 4'- aminomethylfluorescein, 4'-N-alkylaminomethylfluorescein, 5-aminomethylfluorescein, 6-aminomethylfluorescein, 2-4-dichloro-1,3,5-triazin-2-yl-aminofluorescein, 4-chloro-6-methoxy-1,3,5-triazin-2yl-aminofluorescein and fluorescein isothiocyanate.

6. The method according to claim 4 wherein said fluorescein derivative is aminomethylfluorescein.

7. The method according to claim 4 wherein said fluorescein derivative is 5-carboxyfluorescein.

8. The method according to claim 1 wherein said labeled antibody complexes formed are measured by a fluorescence polarization immunoassay wherein the complexes formed in step (b) are excited with polarized light and the polarization of the fluorescence emitted by free tracer and tracer-antibody complexes is measured.

9. The method according to claim 1 wherein step (a) further comprises adding to the test sample to prevent non-specific binding to proteins, a compound of the following structure

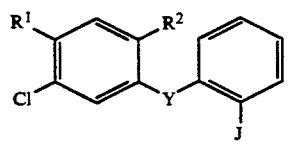

wherein $Y=O$, $R^1=Cl$, $R^2=H$ and $J=CH_2CO_2H$.

10. A kit for detecting the presence or amount of an analyte comprising polychlorinated biphenyl in a test sample which kit comprises
a. an analyte-specific antibody;
b. a tracer having the general structure of

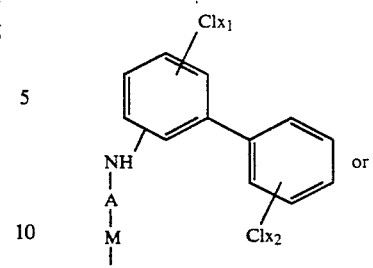

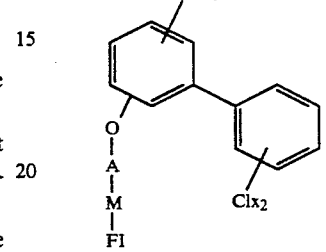

wherein
A is a spacer group consisting of from 0 to 50 carbon atoms and heteroatoms, including not more than ten heteroatoms, arranged in a straight or branched chain, saturated or unsaturated, wherein
  (i) not more than two heteroatoms are linked in the sequence —NH—A—M—Fl or —O—A—M—Fl,
  (ii) A is not a single heteroatom, and
  (iii) branching occurs only on carbon atoms;
M is a linking group selected from the group consisting of

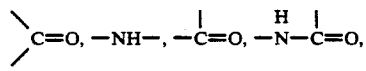

and

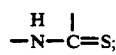

Fl is a detectable moiety;
independently $x_1=0-4$ and $x_2=0-5$, with the proviso that together $x_1$ and $x_2 \geq 1$; and
c. an additive compound which prevents non-specific binding of the analyte to proteins.

11. The kit according to claim 10 wherein the antibody of step (a) is polyclonal or monoclonal.

12. The kit according to claim 10 wherein the detectable moiety attached to the tracer is selected from the group consisting of fluorescein and fluorescein derivatives.

13. The kit according to claim 10 wherein said additive compound has the structure

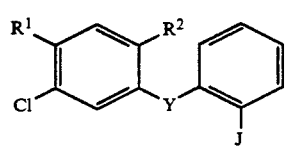

wherein $Y=O$, $R^1=Cl$, $R^2=H$ and $J=CH_2CO_2H$.

* * * * *